United States Patent
Deisseroth et al.

(10) Patent No.: US 10,711,242 B2
(45) Date of Patent: Jul. 14, 2020

(54) APPARATUS AND METHODS FOR CONTROLLING CELLULAR DEVELOPMENT

(75) Inventors: Karl Deisseroth, Palo Alto, CA (US); Albrecht Stroh, Munich (DE); M. Bret Schneider, Portola Valley, CA (US); Raag D. Airan, Menlo Park, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 559 days.

(21) Appl. No.: 12/997,140

(22) PCT Filed: Jun. 17, 2009

(86) PCT No.: PCT/US2009/047701
§ 371 (c)(1),
(2), (4) Date: Feb. 7, 2011

(87) PCT Pub. No.: WO2009/155369
PCT Pub. Date: Dec. 23, 2009

(65) Prior Publication Data
US 2011/0159562 A1     Jun. 30, 2011

Related U.S. Application Data

(60) Provisional application No. 61/093,086, filed on Aug. 29, 2008, provisional application No. 61/132,163, filed on Jun. 17, 2008.

(51) Int. Cl.
*C12N 13/00* (2006.01)
*C12N 5/0735* (2010.01)
(Continued)

(52) U.S. Cl.
CPC ......... *C12N 5/0606* (2013.01); *A61N 5/0601* (2013.01); *C12M 21/02* (2013.01);
(Continued)

(58) Field of Classification Search
None
See application file for complete search history.

(56) References Cited

U.S. PATENT DOCUMENTS 2,968,302 A    1/1961   Fry et al.
3,131,690 A    5/1964   Innis et al.
(Continued)

FOREIGN PATENT DOCUMENTS

CN    1079464 A    12/1993
CN    1558222 A    12/2004
(Continued)

OTHER PUBLICATIONS

Kazutoshi Takahashi and Shinya Yamanaka, Induction of Pluripotent Stem Cells from Mouse Embryonic and Adult Fibroblast Cultures by Defined Factors, 2006, Cell 126, 663-676.*
(Continued)

*Primary Examiner* — Thomas J. Visone
*Assistant Examiner* — Trent R Clarke
(74) *Attorney, Agent, or Firm* — Paula A. Borden; Rudy J. Ng; Bozicevic, Field & Francis LLP

(57) ABSTRACT

According to one aspect and example, a method for facilitating cellular interactions in biological tissue provides controllable activation of a selected type of stem cell among a plurality of cell types present in the tissue. The method includes various steps including the introduction of a microbial opsin into a region of the tissue that includes a selected type of stem cell, by expressing the microbial opsin in the stem cell. A light source is then introduced near the stem cell, and the light source is used to controllably activate the light source to direct pulses of illumination from the light source to the selected type of stem cell, for selectively (Continued)

controlling the growth and development of the stem cell in a manner that is independent of the growth and development of the other types of cells.

18 Claims, 11 Drawing Sheets

(51) Int. Cl.
  *C12N 5/0793* (2010.01)
  *A61N 5/06* (2006.01)
  *C12M 1/00* (2006.01)
  *C12N 15/86* (2006.01)

(52) U.S. Cl.
  CPC ........... *C12N 5/0619* (2013.01); *C12N 15/86* (2013.01); *C12N 2500/38* (2013.01); *C12N 2501/115* (2013.01); *C12N 2501/119* (2013.01); *C12N 2501/385* (2013.01); *C12N 2501/41* (2013.01); *C12N 2501/998* (2013.01); *C12N 2506/02* (2013.01); *C12N 2510/00* (2013.01); *C12N 2529/10* (2013.01); *C12N 2535/00* (2013.01); *C12N 2740/00043* (2013.01)

(56) References Cited

U.S. PATENT DOCUMENTS

| | | |
|---|---|---|
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Kim et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Brown et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,696,722 B2 | 4/2014 | Deisseroth et al. |
| 8,716,447 B2 | 5/2014 | Deisseroth et al. |
| 8,815,582 B2 | 8/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 9,057,734 B2 | 6/2015 | Cohen |
| 9,079,940 B2 | 7/2015 | Deisseroth et al. |
| 9,175,095 B2 | 11/2015 | Deisseroth et al. |
| 9,309,296 B2 | 4/2016 | Deisseroth et al. |
| 9,340,589 B2 | 5/2016 | Deisseroth et al. |
| 9,421,258 B2 | 8/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 9,636,380 B2 | 5/2017 | Deisseroth et al. |
| 9,850,290 B2 | 12/2017 | Deisseroth et al. |
| 9,968,652 B2 | 5/2018 | Deisseroth et al. |
| 10,064,912 B2 | 9/2018 | Deisseroth et al. |
| 10,071,132 B2 | 9/2018 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |

(56) References Cited

U.S. PATENT DOCUMENTS

| | | |
|---|---|---|
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0103949 A1 | 6/2003 | Carpenter et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0260367 A1 | 12/2004 | Taboada et al. |
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |
| 2005/0102708 A1 | 5/2005 | Lecanu et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0129126 A1 | 6/2006 | Kaplitt et al. |
| 2006/0155348 A1 | 7/2006 | deCharms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Iyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand et al. |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0088680 A1 | 4/2009 | Aravanis et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0148861 A1 | 6/2009 | Pegan et al. |
| 2009/0157145 A1 | 6/2009 | Cauller |
| 2009/0069261 A1 | 10/2009 | Nikolov et al. |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Zhang et al. |
| 2010/0209352 A1 | 8/2010 | Hultman et al. |
| 2010/0234273 A1 | 9/2010 | Boyden et al. |
| 2011/0021270 A1 | 1/2011 | Vo-Dinh et al. |
| 2011/0092800 A1 | 4/2011 | Yoo et al. |
| 2011/0105998 A1 | 5/2011 | Zhang et al. |
| 2011/0112179 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0165681 A1 | 7/2011 | Boyden et al. |
| 2011/0166632 A1 | 7/2011 | Delp et al. |
| 2011/0172653 A1 | 7/2011 | Deisseroth et al. |
| 2011/0224095 A1 | 9/2011 | Zoller et al. |
| 2011/0233046 A1 | 9/2011 | Nikolenko et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0190629 A1 | 7/2012 | Tomita et al. |

(56) References Cited

U.S. PATENT DOCUMENTS

| | | |
|---|---|---|
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0066402 A1 | 3/2013 | Lin et al. |
| 2013/0144359 A1 | 6/2013 | Kishawi et al. |
| 2013/0286181 A1 | 10/2013 | Betzig et al. |
| 2015/0112411 A1 | 4/2015 | Beckman et al. |

FOREIGN PATENT DOCUMENTS

| | | |
|---|---|---|
| CN | 101288768 A | 10/2008 |
| CN | 102076866 A | 5/2011 |
| CN | 103313752 A | 9/2013 |
| CN | 103476456 A | 12/2013 |
| EP | 1197144 | 4/2002 |
| EP | 1 334 748 | 8/2003 |
| EP | 1444889 | 8/2004 |
| EP | 1873566 | 1/2008 |
| JP | 2006-295350 | 10/1994 |
| JP | H 09505771 A | 6/1997 |
| JP | 2004534508 | 11/2004 |
| JP | 2005034073 A | 2/2005 |
| JP | 2006217866 | 8/2006 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001-025466 | 4/2001 |
| WO | WO 03/106486 A2 | 2/2003 |
| WO | WO 2003/016486 | 2/2003 |
| WO | WO 2003-040323 | 5/2003 |
| WO | WO 2003/046141 | 6/2003 |
| WO | WO 2003-84994 | 10/2003 |
| WO | WO 2003-102156 | 12/2003 |
| WO | WO 2004/033647 | 4/2004 |
| WO | WO 2005/093429 | 10/2005 |
| WO | WO 2006/103678 | 10/2006 |
| WO | WO 2007-024391 | 3/2007 |
| WO | WO 2007-131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO2009/119782 | 10/2009 |
| WO | WO 2009-131837 | 10/2009 |
| WO | WO 2009/148946 | 12/2009 |
| WO | WO 2010/006049 | 1/2010 |
| WO | WO 2010/011404 A3 | 1/2010 |
| WO | WO 2010/056970 | 5/2010 |
| WO | WO-2010123993 | 10/2010 |
| WO | WO 2011/005978 | 1/2011 |
| WO | WO 2011/066320 A3 | 6/2011 |
| WO | WO 2011/106783 | 9/2011 |
| WO | WO 2011-116238 A2 | 9/2011 |
| WO | WO 2011/127088 A3 | 10/2011 |
| WO | WO 2012/032103 | 3/2012 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061741 | 5/2012 |
| WO | WO 2012/061744 | 5/2012 |
| WO | 2012/106407 | 8/2012 |
| WO | WO 2012/134704 A2 | 10/2012 |
| WO | WO 2013/003557 | 1/2013 |
| WO | WO 2013/090356 | 6/2013 |
| WO | WO 2013/126762 | 8/2013 |
| WO | WO 2014/081449 | 5/2014 |
| WO | WO 2014/117079 | 7/2014 |
| WO | WO 2015/148974 | 10/2015 |
| WO | WO 2016/019075 | 2/2016 |
| WO | WO 2016/090172 | 6/2016 |
| WO | WO 2017/087542 | 5/2017 |

OTHER PUBLICATIONS

Bridget C. Loetterle, Maisie Rogers, Tina Valdner, Carmen Mason, Ina Christian, Wayne Andreesen, Cerebellar Stimulation: Pacing the Brain, 1975, The American Journal of Nursing, vol. 75, No. 6, pp. 958-960.*

Morelli et al., Neuronal and glial cell type-specific promoters within adenovirus recombinants restrict the expression of the apoptosis-inducing molecule Fas ligand to predetermined brain cell types, and abolish peripheral liver toxicity, 1999, Journal of General Virology (1999), 80, 571-583.*

Cazillis M, Gonzalez BJ, Billardon C, Lombet A, Fraichard A, Samarut J, Gressens P, Vaudry H, Rostene W, VIP and PACAP induce selective neuronal differentiation of mouse embryonic stem cells, Eur J Neurosci, Feb. 2004;19(4):798-808, Abstract only.*

De Foubert et al. " Fluoxetine-Induced Change in Rat Brain Expression of Brain-Derived Neurotrophic Factor Varies Depending on Length of Treatment," Neuroscience, 2004, vol. 128, pp. 597-604.

Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.

Gold, et al. "Representation of a perceptual decision in developing oculomotor commands", Nature, 2000, vol. 404, pp. 390-394.

Gregory, et al. "Integration site for Streptomyces phage φBT1 and development of site-specific integrating vectors", Journal of Bacteriology, 2003, vol. 185, No. 17, pp. 5320-5323.

Gulick, et al. "Transfection using DEAE-Dextran" Supplement 40, Current Protocols in Molecular Biology, 1997, Supplement 40, 9.2.1-9.2.10.

Hausser, et al. "Tonic Synaptic Inhibition Modulates Neuronal Output Pattern and Spatiotemporal Synaptic Integration", Neuron, 1997, vol. 19, pp. 665-678.

Kingston et al. "Transfection and Expression of Cloned DNA," Supplement 31, Current Protocols in Immunology, 1999, 10.13.1-10.13.9.

Louis et al. "Cloning and sequencing of the cellular-viral junctions from the human adenovirus type 5 transformed 293 cell line," Virology, 1997, vol. 233, pp. 423-429.

Mortensen et al. "Selection of Transfected Mammalian Cells," Supplement 86, Current Protocols in Molecular Biology, 1997, 9.5.1-09.5.19.

Pear "Transient Transfection Methods for Preparation of High-Titer Retroviral Supernatants" Supplement 68, Current Protocols in Molecular Biology, 1996, 9.1 1 .1-9.1 1 .1 8.

Pouille, et al. "Routing of spike series by dynamic circuits in the hippocampus", Nature, 2004, vol. 429: pp. 717-723.

Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.

Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.

Song, "Genes responsible for native depolarization-activated K+ currents in neurons," Neuroscience Research, 2002, vol. 42, pp. 7-14.

Wells et al. "Application of Infrared light for in vivo neural stimulation," Journal of Biomedical Optics, 2005, vol. 10(6), pp. 064003-1-064003-12.

Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.

Gonzalez, et al., "Cell-Based Assays and Instrumentation for Screening Ion-Channel Targets", DDT, 1999, vol. 4, No. 9, pp. 431439.

(56) References Cited

OTHER PUBLICATIONS

Natochin, et al. "Probing rhodopsin-transducin interaction using *Drosophila* Rh1-bovine rhodopsin chimeras," Vision Res., 2006, vol. 46, No. 27: pp. 4575-4581.
Peterlin, et al. "Optical probing of neuronal circuits with calcium indicators," PNAS, 2000, vol. 97, No. 7: pp. 3619-3624.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ahmad, et al. "The *Drosophila* rhodopsin cytoplasmic tail domain is required for maintenance of rhabdomere structure." The FASEB Journal, 2007, vol. 21, p. 449-455.
Akirav, et al. "The role of the medial prefrontal cortex-amygdala circuit in stress effects on the extinction of fear", Neural Plasticity, 2007: vol. 2007 Article ID:30873, pp. 1-11.
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Argos, et al. "The integrase family of site-specific recombinases: regional similarities and global diversity", The EMBO Journal, 1986, vol. 5, No. 2, pp. 433-440.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Basil et al. "Is There Evidence for Effectiveness of Transcranial Magnetic Stimulation in the Treatment of Psychiatric Disorders?" Psychiatry, 2005, pp. 64-69.
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berridge et al., "The Versatility and Universality of Calcium Signaling", Nature Reviews: Molecular Cell Biology, 2000, vol. 1: pp. 11-21.
Bocquet et al. "A prokaryotic proton-gated ion channel from the nicotinic acetylcholine receptor family." Nature Letters, 2007, vol. 445, p. 116-119.
Boyden, et al. "Millisecond-timescale, genetically targeted optical control of neural activity" Nature Neuroscience, 2005, vol. 8, No. 9: pp. 1263-1268.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-10472.
Blomer et al., "Highly Efficient and Sustained Gene Transfer in Adult Neurons with Lentivirus Vector", Journal of Virology,1997, vol. 71, No. 9: pp. 6641-6649.
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.

Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." the Journal of Neuroscience, 2000, vol. 20, No. 21, pp. 7880-7887.
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cenatiempo "Prokaryotic gene expression in vitro: transcription-translation coupled systems", Biochimie, 1986, vol. 68(4): pp. 505-515.
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Crouse, et al. "Expression and amplification of engineered mouse dihydrofolate reductase minigenes" Mol. Cell. Biol. , 1983, vol. 3(2): pp. 257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cucchiaro et al., "Electron-Microsoft Analysis of Synaptic Input from the Perigeniculate Nucleus to A-Lamine of the Lateral Geniculate Nucleus in Cats", The Journal of Comparitive Neurology, 1991, vol. 310, pp. 316-336.
Cui, et al., "Electrochemical deposition and characterization of conducting polymer polypyrrole/PSS on multichannel neural probes," Sensors and Actuators, 2001, vol. 93(1): pp. 8-18.
Date, et al. "Grafting of Encapsulated Dopamine-Secreting Cells in Parkinson's Disease: Long-Term Primate Study", Cell Transplant, 2000, vol. 9, pp. 705-709.
Dalva, et al. "Rearrangements of Synaptic Connections in Visual Cortex Revealed by Laser Photostimulation", Science, 1994,vol. 265, pp. 255-258.
Dederen, et al. "Retrograde neuronal tracing with cholera toxin B subunit: comparison of three different visualization methods", Histochemical Journal, 1994, vol. 26, pp. 856-862.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Translocation of Calmodulin to the Nucleus Supports CREB Phosphorylation in Hippocampal Neurons", Nature, 1998, vol. 392, pp. 198-202.
Deisseroth et al., "Signaling from Synapse to Nucleus: the logic Behind the Mechanisms", Currrent Opinion in Neurobiology, 2003, vol. 13, pp. 354-365.
Deisseroth "Next-generation optical technologies for illuminating genetically targeted brain circuits," The Journal of Neuroscience, 2006, vol. 26, No. 41, pp. 10380-10386.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Ensell, et al. "Silicon-based microelectrodes for neurophysiology, micromachined from silicon-on-insulator wafers," Med. Biol. Eng. Comput., 2000, vol. 38, pp. 175-179.

(56) References Cited

OTHER PUBLICATIONS

Eisen, "Treatment of amyotrophic lateral sclerosis", Drugs Aging, 1999; vol. 14, No. 3, pp. 173-196.
Evanko "Optical excitation yin and yang" Nature Methods, 2007, 4:384.
Esposito et al. "The integrase family of tyrosine recombinases: evolution of a conserved active site domain", Nucleic Acids Research, 1997, vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Gelvich et al. "Contact flexible microstrip applicators (CFMA) in a range from microwaves up to short waves," IEEE Transactions on Biomedical Engineering, 2002, vol. 49, Issue 9: 1015-1023.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat ", Neuroscience, 1997, vol. 76, No. 3, pp. 689-706.
Gottesman et al."Bacterial regulation: global regulatory networks," Ann. Rev. Genet., 1984, vol. 18, pp. 415-441.
Greenberg, et al. "Three-year outcomes in deep brain stimulation for highly resistant obsessive-compulsive disorder," Neuropsychopharmacology, 2006, vol. 31, pp. 2384-2393.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol., 2005, vol. 94, pp. 3069-3080.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.

Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hegemann et al., "All-trans Retinal Constitutes the Functional Chromophore in *Chlamydomonas* rhodopsin", Biophys. J., 1991, vol. 60, pp. 1477-1489.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane, " PNAS, 1993, vol. 90, pp. 3578-3582.
Hirase, et al. "Multiphoton stimulation of neurons", J Neurobiol, 2002, vol. 51, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hosokawa, T. et al. "Imaging spatio-temporal patterns of long-term potentiation in mouse hippocampus." Philos. Trans. R. Soc. Lond. B., 2003, vol. 358, pp. 689-693.
Hynynen, et al. "Clinical applications of focused ultrasound-The brain." Int. J. Hyperthermia, 2007, vol. 23, No. 2: pp. 193-202.
International Search Report for International Application No. PCT/US2009/053474, dated Oct. 8, 2009.
Isenberg et al. "Cloning of a Putative Neuronal Nicotinic Aceylcholine Receptor Subunit," Journal of Neurochemistry, 1989, pp. 988-991.
Johnston et al. "Isolation of the yeast regulatory gene GAL4 and analysis of its dosage effects on the galactose/melibiose regulon," PNAS, 1982, vol. 79, pp. 6971-6975.
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khossravani et al., "Voltage-Gated Calcium Channels and Idiopathic Generalized Epilepsies", Physiol. Rev., 2006, vol. 86: pp. 941-966.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.

(56) References Cited

OTHER PUBLICATIONS

Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Landy, A. "Mechanistic and structural complexity in the site-specific recombination pathways of Int and FLP", Current Opinion in Genetics and Development, 1993, vol. 3, pp. 699-707.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gone Therapy Can Prevent Neuron Deatch Resulting from Necrotic and Apoptotic Insults", Journal of Neurochemistry, 2003, vol. 85: pp. 1079-1088.
Levitan et al. "Surface Expression of Kv1 Voltage-Gated K+ Channels is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mcknight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Monje et al., "Irradiation Induces Neural Precursor-Cell Dysfunction", Natural Medicine, 2002, vol. 8, No. 9, pp. 955-962.
Nacher, et al. "NMDA receptor antagonist treatment increases the production of newneurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Nirenberg, et al. "The Light Response of Retinal Ganglion Cells is Truncated by a Displaced Amacrine Circuit", Neuron, 1997, vol. 18: pp. 637-650.
Nunes-Duby, et al. "Similarities and differences among 105 members of the Int family of site-specific recombinases" , Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Palmer et al., "The Adult Rat Hippocampus Contains Primordial Neural Stem Cells", Molecular and Cellular Neuroscience, 1997, vol. 8, pp. 389-404.
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Pan et al. "Functional Expression of a Directly Light-Gated Membrane Channel in Mammalian Retinal Neurons: A Potential Strategy for Restoring Light Sensitivity to the Retina After Photoreceptor Degeneration," Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Potter, "Transfection by Electroporation." Supplement 62, Current Protocols in Molecular Biology, 1996, 9.3.1-9.3.6.
Qiu et al. "Induction of photosensitivity by heterologous expression of melanopsin", Nature, 2005, vol. 433: pp. 745-749.
Rathnasingham et al., "Characterization of implantable microfabricated fluid delivery devices," IEEE Transactions on Biomedical Engineering, 2004, vol. 51, No. 1: pp. 138-145.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.

(56) References Cited

OTHER PUBLICATIONS

Rudiger et at. "Specific arginine and threonine residues control anion binding and transport in the light-driven chloride pump halorhodopsin," The EMBO Journal, 1997, vol. 16, No. 13, pp. 3813-3821.
Salzman, et al. "Cortical microstimulation influences perceptual judgements of motion direction", Nature, 1990, vol. 346, pp. 174-177.
Sato et al. "Role of Anion-binding Sites in cytoplasmic and extracellular channels of Natronomonas pharaonis halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008,vol. 33, pp. 368-377.
Sclimenti, et al. "Directed evolution of a recombinase for improved genomic integration at a native human sequence," Nucleic Acids Research, 2001, vol. 29, No. 24: pp. 5044-5051.
Shepherd, et al. "Circuit Analysis of Experience-Dependent Plasticity in the Developing Rat Barrel Cortex", Neuron, 2003, vol. 38: pp. 277-289.
Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.
Silver, et al. "Amino terminus of the yeast GAL4 gene product is sufficient for nuclear localization" PNAS, 1984, vol. 81, No. 19: pp. 5951-5955.
Singer et al. "Elevated Intrasynaptic Dopamine Release in Tourette's Syndrome Measured by PET," American Journal of Psychiatry, 2002, vol. 159: pp. 1329-1336.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Takahashi, et al."Diversion of the Sign of Phototaxis in a Chlamydomonas reinhardtii Mutant Incorporated with Retinal and Its Analogs," FEBS Letters, 1992, vol. 314, No. 3, pp. 275-279.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Tsau et al. "Distributed Aspects of the Response to Siphon Touch in Aplysia: Spread of Stimulus Information and Cross-Correlation Analysis," The Journal of Neuroscience, 1994, vol. 14, No. 7, pp. 4167-4184.
[No Authors Listed] "Two bright new faces in gene therapy," Nature Biotechnology, 1996, vol. 14: p. 556.
Tye et. al. "Amygdala circuitry mediating reversible and bidirectional control of anxiety", Nature, 2011, vol. 471(7338): pp. 358-362.

Tye et. al., Supplementary Materials: "An optically-resolved microcircuit for bidirectional anxiety control", Nature, 2011, vol. 471(7338): pp. 358-362.
Ulmanen, et al. "Transcription and translation of foreign genes in Bacillus subtilis by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:19.1-19.39.
Ward, et al. "Construction and characterisation of a series of multi-copy promoter-probe plasmid vectors for Streptomyces using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Wang et al. "Direct-current Nanogenerator Driven by Ultrasonic Waves," Science, 2007, vol. 316, pp. 102-105.
Wang et. al., "High-speed mapping of synaptic connectivity using photostimulation in Channelrhodopsin-2 transgenic mice", PNAS, 2007, vol. 104, No. 19, pp. 8143-8148.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Witten et. al., Supporting Online Material for: "Cholinergic Interneurons Control Local Circuit Activity and Cocaine Conditioning", Science, 2010, vol. 330: 17 pages.
Witten et. al., "Cholinergic Interneurons Control Local Circuit Activity and Cocaine Conditioning", Science, 2010, vol. 330, No. 6011: pp. 1677-1681.
Yamazoe, et al. "Efficient generation of dopaminergic neurons from mouse embryonic stem cells enclosed in hollow fibers", Biomaterials, 2006, vol. 27, pp. 4871-4880.
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang, et al. "Channelrhodopsin-2 and optical control of excitable cells," Nature Methods,2006, vol. 3, No. 10, pp. 785-792.
Zhang, et al. "Red-Shifted Optogenetic Excitation: a Tool for Fast Neural Control Derived from Volvox carteri", Nature Neurosciences, 2008,vol. 11, No. 6, pp. 631-633.
Zhang "Multimodal fast optical interrogation of neural circuitry," Nature, 2007, vol. 446, pp. 633-641.
Zrenner, E., "Will Retinal Implants Restore Vision?" Science, 2002, vol. 295, No. 5557, pp. 1022-1025.

(56) References Cited

OTHER PUBLICATIONS

Zufferey, et al. "Self-Inactivating Lentivirus Vector for Safe and Efficient In Vivo Gene Delivery", Journal of Virology, 1998, vol. 72, No. 12, pp. 9873-9880.
Tye, et al. "Optogenetic investigation of neural circuits underlying brain disease in animal models," Nature Reviews Neuroscience (Mar. 2012), 13(4):251-266.
Airan, et al., "Temporally Precise in vivo Control of Intracellular Signaling", 2009, Nature, vol. 458, No. 7241, pp. 1025-1029.
Braun, "Two Light-activated Conductances in the Eye of the Green Alga *Volvox carteri*", 1999, Biophys J., vol. 76, No. 3, pp. 1668-1678.
Cardin, et al. "Driving Fast spiking Cells Induces Gamma Rhythm and Controls Sensory Responses", 2009, Nature, vol. 459, vol. 7247, pp. 663-667.
Deisseroth et al., "Excitation-neurogenesis Coupling in Adult Neural Stem/Progenitor Cells", 2004, Neuron, vol. 42, pp. 535-552.
Ernst, et al. "Photoactivation of Channelrhodopsin", 2008, vol. 283, No. 3, pp. 1637-1643.
Genbank Accession No. DQ094781 (Jan. 15, 2008).
Gradinaru, et al. "ENpHR: a Natronomonas Halorhodopsin Enhanced for Optogenetic Applications", 2008, Brain Cell Biol., vol. 36 (1-4), pp. 129-139.
Herlitze, et al., "New Optical Tools for Controlling Neuronal Activity", 2007, Curr Opin Neurobiol, vol. 17, No. 1, pp. 87-94.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
Mcallister, "Cellular and Molecular Mechanisms of Dendrite Growth", 2000, Cereb Cortex, vol. 10, No. 10, pp. 963-973.
Pape, et al., "Plastic Synaptic Networks of the Amygdala for the Acquisition, Expression, and Extinction of Conditioned Fear", 2010, Physiol Rev, vol. 90, pp. 419-463.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Ritter, et al., "Monitoring Light-induced Structural Changes of Channelrhodopsin-2 by UV-Visable and Fourier Transform Infared Spectroscopy", 2008, The Journal of Biological Chemistry, vol. 283, No. 50, pp. 35033-35041.
Sajdyk, et al., "Excitatory Amino Acid Receptors in the Basolateral Amygdala Regulate Anxiety Responses in the Social Interaction Test", Brain Research, 1997, vol. 764, pp. 262-264.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
"SubName: Full=Channelrhodopsin-1", retrieved from EBI accession No. UNIPROT: B4Y103. Database accession No. B4Y103. Sep. 23, 2008.
Tam, B. et al., "Identification of an Outer Segment Targeting Signal in the COOH Terminus of Rhodopsin Using Transgenic Xenopus laevis", The Journal of Cell Biology, 2000, vol. 151, No. 7, pp. 1369-1380.
U.S. Appl. No. 13/299,727, filed Nov. 18, 2011, Lee, et al.
U.S. Appl. No. 11/459,636, filed Jul. 24, 2006, published as US 2007-0261127.
U.S. Appl. No. 11/459,638, filed Jul. 24, 2006, published as US 2007-0054319.
U.S. Appl. No. 11/651,422, filed Jan. 9, 2007, published as US 2008-0085265.
U.S. Appl. No. 12/031,651, filed Feb. 14, 2008, published as US 2008-0227139.
U.S. Appl. No. 12/185,624, filed Aug. 4, 2008, published as US 2009-0088680.
U.S. Appl. No. 12/187,927, filed Aug. 7, 2008, published as US 2009-0099038.
U.S. Appl. No. 12/263,026, filed Oct. 31, 2008, published as US 2009-0112133.
U.S. Appl. No. 12/263,044, filed Oct. 31, 2008, published as US 2009-0118800.
U.S. Appl. No. 12/522,520, filed Jan. 8, 2010, published as US 2010-0145418.
U.S. Appl. No. 12/522,528, filed Apr. 6, 2010, published as US 2010-0190229.
U.S. Appl. No. 12/715,259, filed Mar. 1, 2010, published as US 2010-0234273.
U.S. Appl. No. 12/988,567, filed Dec. 7, 2010, published as US 2011-0105998.
U.S. Appl. No. 12/993,605, filed Jan. 20, 2011, published as US 2011-0112179.
U.S. Appl. No. 12/996,753, filed Mar. 10, 2011, published as US 2011-0166632.
U.S. Appl. No. 12/997,158, filed Feb. 7, 2011, published as US 2011-0172653.
U.S. Appl. No. 13/128,979, filed Jul. 28, 2011, published as US 2011-0311489.
U.S. Appl. No. 13/208,419, filed Aug. 12, 2011, published as US 2011-0301529.
U.S. Appl. No. 13/299,727, filed Nov. 18, 2011.
Fox et al., "A gene neuron expression fingerprint of C. elegans embryonic motor neurons", BMC Genomics, 2005, 6(42):1-23.
Nonet, "Visualization of synaptic specializations in live C. elegans with synaptic vesicle protein-GFP fusions", J. Neurosci. Methods, 1999, 89:33-40.
Synapse, Chapter 13, http://michaeldmann.net/mann13.html, downloaded Apr. 2014.
Hikida et al., "Increased sensitivity to cocaine by cholinergic cell ablation in nucleus accumbens", PNAS, Nov. 2001, 98(23): 13351-13354.
Hikida et al., "Acetylcholine enhancement in the nucleus accumbens prevents addictive behaviors of cocaine and morphine", PNAS, May 2003, 100(10):6169-6173.
Kitabatake et al., "Impairment of reward-related learning by cholinergic cell ablation in the striatum", PNAS, Jun. 2003, 100(13):7965-7970.
Tamai, "Progress in Pathogenesis and Therapeutic Research in Retinitis Pigmentosa and Age Related Macular Degeneration", Nippon Ganka Gakkai Zasshi, vol. 108, No. 12, Dec. 2004 (Dec. 2004), pp. 750-769.
Fiala et al., "Optogenetic approaches in neuroscience", Current Biology, Oct. 2010, 20(20): R897-R903.
Gradinaru et al., "Optical deconstruction of parkinsonian neural circuitry", Science, Apr. 2009, 324(5925):354-359.
Liu et al., "Optogenetics 3.0", Cell, Apr. 2010, 141(1):22-24.
Malin et al., "Involvement of the rostral anterior cingulate cortex in consolidation of inhibitory avoidance memory: Interaction with the basolateral amygdala", Neurobiol Learning Mem, 2007, 87(2):295-302.
Mayford et al., "Control of memory formation through regulated expression of CAMKII Transgene", Science, Dec. 1996, 274:1678-1683.
Schroll et al., "Light-induced activation of distinct modulatory neurons triggers appetitive or aversive learning in *Drosophila* larvae", Current Biology, Sep. 2006, 16(17):1741-1747.
Gradinaru, et al., Molecular and Cellular Approaches for Diversifying and Extending Optogenetics, Cell, 2010, vol. 141, No. 1, pp. 154-165.
RecName: Full=Halorhodopsin; Short=HR; Alt Name: Full=NpHR; XP002704922, retrieved from EBI accession No. UNIPROT: P15647. Database accession No. P15647. Apr. 1, 1990.

(56) References Cited

OTHER PUBLICATIONS

"N. pharaonis halorhodopsin (hop) gene, complete cds.", XP002704883, retrieved from EBI accession No. EMBL: J05199. Database accession No. J05199. Nov. 22, 1990.
"Subname: Fluu=Bacteriorhodopsin"; XP002704863, retrieved from EBI accession No. UNIPROT: B0R5N9. Database accession No. B0R5N9. Apr. 8, 2008.
Zhang, et al., "The Microbial Opsin Family of Optogenetic Tools", Cell, 2011, vol. 147, No. 7, pp. 1146-1457.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
Lanyi et al. "The primary structure of a Halorhodopsin from *Natronobacterium pharaonis*" Journal of Biological Chemistry 1990, vol. 265, No. 3, p. 1253-1260.
Hofherr et al. "Selective Golgi export of Kir2.1 controls the stoichiometry of functional Kir2.x channel heteromers"Journal of Cell Science, 2005, vol. 118, p. 1935-1943.
Xiong et al., "Interregional connectivity to primary motor cortex revealed using MRI resting state images", Hum Brain Mapp, 1999, 8(2-3):151-156.
Arenkiel, et al. "In vivo light-induced activation of neural circuitry in transgenic mice expressing Channelrhodopsin-2", Neuron, 2007, 54:205-218.
Milella et al. "Opposite roles of dopamine and orexin in quinpirole-induced excessive drinking: a rat model of psychotic polydipsia" Psychopharmacology, 2010, 211:355-366.
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Balint, et al., "The Nitrate Transporting Photochemical Reaction Cycle of the Pharaonis Halorhodopsin", Biophysical Journal, 2004, vol. 86, pp. 1655-1663.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Definition of Psychosis (2015).
Ebert et al., "A Moloney MLV-rat somatotropin fusion gene produces biologically active somatotropin in a transgenic pig", Mol. Endocrinology, 1988, vol. 2, pp. 277-283.

Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Karra, et al. "Transfection Techniques for Neuronal Cells", The Journal of Neuroscience, 2010, vol. 30, No. 18, pp. 6171-6177.
Kelder et al., "Glycoconjugates in human and transgenic animal milk", Advances in Exp. Med. and Biol., 2001, vol. 501, pp. 269-278.
Mullins et al., "Fulminant hypertension in transgenic rats harbouring the mouse Ren-2 gene", Nature, 1990, vol. 344, pp. 541-544.
Mullins et al., "Expression of the DBA/2J Ren-2 gene in the adrenal gland of transgenic mice", EMBO, 1989, vol. 8, pp. 4065-4072.
Taurog et al., "HLA-B27 in inbred and non-inbred transgenic mice", J. Immunol., 1988, vol. 141, pp. 4020-4023.
Wall, "Transgenic livestock: Progress and prospects for the future", Theriogenology, 1996, vol. 45, pp. 57-68.
Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.
Written opinion of PCT Application No. PCT/US2011/059383 (dated May 9, 2012).
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Cazillis et al., "VIP and PACAP induce selective neuronal differentiation of mouse embryonic stem cells", Eur J Neurosci, 2004, 19(4):798-808.
Davis; "The many faces of epidermal growth factor repeats," The New Biologist; vol. 2, No. 5, pp. 410-419 (1990).
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
EBI accession No. UNIPROT: A7U0Y6; "SubName: Full= Bacteriorhodopsin"; (Aug. 10, 2010).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
Kaiser; "Clinical research. Death prompts a review of gene therapy vector"; Science; 317(5838):580 (Aug. 3, 2007).
Kay; "State-of-the-art gene-based therapies: the road ahead"; Nature Reviews Genetics; vol. 12, pp. 316-328 (May 2011).
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Berke, et al. "Addiction, Dopamine, and the Molecular Mechanisms of Memory", Molecular Plasticity, 2000, vol. 25: pp. 515-532.
Goshen et al. "Dynamics of Retrieval Strategies for Remote Memories", Cell, 2011, vol. 147: pp. 678-589.
Jimenez S.A & Maren S. et al/ "Nuclear disconnection within the amygdala reveals a direct pathway to fear", Learning Memory, 2009, vol. 16: pp. 766-768.
Ehrlich I. et al. "Amygdala inhibitory circuits and the control of fear memory", Neuron, 2009. Friedrich Meischer Institute, vol. 62: pp. 757-771.
Berndt et al. "Bi-stable neural state switches", Nature Neuroscience, 2009, vol. 12, No. 2: pp. 229-234.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Brewin; "The Nature and Significance of Memory Disturbance in Posttraumatic Stress Disorder"; Ann. Rev. Clin. Psychol.; vol. 7, pp. 203-227 (2011).

(56) References Cited

OTHER PUBLICATIONS

Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).

Samuelson; "Post-traumatic stress disorder and declarative memory functioning: a review"; Dialogues in Clinical Neuroscience; vol. 13, No. 3, pp. 346-351 (2011).

Gradinaru et al., "Targeting and readout strategies for fast optical neural control in vitro and in vivo", J Neuroscience, 2007, 27(52):14231-14238.

Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.

Fenno et al., "The development and application of optogenetics", Annual Review of Neuroscience, 2011, vol. 34, No. 1, pp. 389-412.

Gunaydin et al., "Ultrafast optogenetic control", Nature Neuroscience, 2010, vol. 13, No. 3, pp. 387-392.

Hira et al., "Transcranial optogenetic stimulation for functional mapping of the motor cortex", J Neurosci Methods, 2009, vol. 179, pp. 258-263.

Lalumiere, R., "A new technique for controlling the brain: optogenetics and its potential for use in research and the clinic", Brain Stimulation, 2011, vol. 4, pp. 1-6.

Lin, "A user's guide to channelrhodopsin variants: features, limitations and future developments", Exp Physiol, 2010, vol. 96, No. 1, pp. 19-25.

Mancuso et al., "Optogenetic probing of functional brain circuitry", Experimental Physiology, 2010, vol. 96.1, pp. 26-33.

Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.

Pinkham et al., "Neural bases for impaired social cognition in schizophrenia and autism spectrum disorders", Schizophrenia Research, 2008, vol. 99, pp. 164-175.

Sohal et al., "Parvalbumin neurons and gamma rhythms enhance cortical circuit performance", Nature, 2009, vol. 459, No. 7247, pp. 698-702.

Yizhar et al., "Optogenetics in neural systems", Neuron Primer, 2011, vol. 71, No. 1, pp. 9-34.

Li et al., "Surface Expression of Kv1 Channels is Governed by a C-Terminal Motif", J. Bioi. Chem. (2000), 275(16):11597-11602.

Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.

Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.

Deisseroth, et al., "Controlling the Brain with Light", Scientific American, 2010, vol. 303, pp. 48-55.

Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.

Sineshchekov, et al., "Two Rhodopsins Mediate Phototaxis to Low and High Intensity Light in Chlamydomas Reinhardtil", PNAS, 2002, vol. 99, No. 13, pp. 8689-8694.

Tønnese, et al., "Optogenetic Control of Epileptiform Activity", PNAS, 2009, vol. 106, No. 29, pp. 12162-12167.

Berndt et al., "Structure-Guided Transformation of Channelrhodopsin into a Light-Activated Chloride Channel", Science, (Apr. 2014), 344(6182):420-424.

Chow et al., "Optogenetics and Translational Medicine", Science Translational Medicine (Mar. 2013), 5(177):177ps5.

Eijkelkamp, et al. "Neurological perspectives on voltage-gated sodium channels", Brain (Sep. 2012), 135(Pt 9):2585-2612.

Garrido et al., "A targeting motif involved in sodium channel clustering at the axonal initial segment", Science (Jun. 2003), 300(5628):2091-4.

Han; et al., "Two-color, bi-directional optical voltage control of genetically-targeted neurons", CoSyne (2007), Abstract Presentation, Poster III-67, p. 269, Presented Feb. 24, 2007.

Hustler; et al., "Acetylcholinesterase staining in human auditory and language cortices: regional variation of structural features", Cereb Cortex (Mar.-Apr. 1996), 6(2):260-70.

Iyer et al., "Virally mediated optogenetic excitation and inhibition of pain in freely moving nontransgenic mice", Nat Biotechnol., (Mar. 2014), 32(3):274-8.

Ji et al., "Light-evoked Somatosensory Perception of Transgenic Rats that Express Channelrhodopsin-2 in Dorsal Root Ganglion Cells", PLoS One (2012), 7(3):e32699.

Jennings et al., "Distinct extended amygdala circuits for divergent motivational states," Nature (Apr. 2013), 496 (7444):224-8.

Kim et al., "PDZ domain proteins of synapses", Nature Reviews Neuroscience, (Oct. 2004), 5(10):771-81.

Kim et al., "Diverging neural pathways assemble a behavioural state from separable features in anxiety" Nature (Apr. 2013), 496(7444):219-23.

Kokel et al., "Photochemical activation of TRPA1 channels in neurons and animals", Nat Chem Biol (Apr. 2013), 9(4):257-63.

Lammel et al., "Input-specific control of reward and aversion in the ventral tegmental area", Nature (Nov. 2012), 491(7423): 212-7.

Liske et al., "Optical inhibition of motor nerve and muscle activity in vivo", Muscle Nerve (Jun. 2013), 47(6):916-21.

Llewellyn et al., "Orderly recruitment of motor units under optical control in vivo", Nature Medicine, (Oct. 2010), 16(10):1161-5.

Mattis et al., "Principles for applying optogenetic tools derived from direct comparative analysis of microbial opsins", Nat Methods (Dec. 2011), 9(2):159-72.

Mourot et al., "Rapid Optical Control of Nociception with an Ion Channel Photoswitch", Nat Methods (Feb. 2012), 9(4):396-402.

Nieh et al., "Optogenetic dissection of neural circuits underlying emotional valence and motivated behaviors", Brain Research, (May 2012), 1511:73-92.

Slamovits et al., "A bacterial proteorhodopsin proton pump in marie eukaryotes", Nature Communications (Feb. 2011), 2:183.

Towne et al., "Efficient transduction of non-human primate motor neurons after intramuscular delivery of recombinant AAV serotype 6", Gene Ther. (Jan. 2010), 17(1):141-6.

Towne et al., "Optogenetic control of targeted peripheral axons in freely moving animals", PLoS One (Aug. 2013), 8(8):e72691.

Towne et al., "Recombinant adeno-associated virus serotype 6 (rAAV2/6)-mediated gene transfer to nociceptive neurons through different routes of delivery", Mol Pain (Sep. 2009), 5:52.

Wang et al., "Mrgprd-Expressing Polymodal Nociceptive Neurons Innervate Most Known Classes of Substantia Gelatinosa Neurons", J Neurosci (Oct. 2009), 29(42):13202-13209.

Williams et al., "From optogenetic technologies to neuromodulation therapies", Sci Transl Med. (Mar. 2013), 5(177):177ps6.

Babin et al., "Zebrafish Models of Human Motor Neuron Diseases: Advantages and Limitations", Progress in Neurobiology (2014), 118:36-58.

Santana et al., "Can Zebrafish Be Used as Animal Model to Study Alzheimer's Disease?" Am. J. Neurodegener. Dis. (2012), 1(1):32-48.

Sheikh et al., "Neurodegenerative Diseases: Multifactorial Conformational Diseases and Their Therapeutic Interventions", Journal of Neurodegenerative Diseases (2013), Article ID 563481:1-8.

Suzuki et al., "Stable Transgene Expression from HSV Amplicon Vectors in the Brain: Potential Involvement of Immunoregulatory Signals", Molecular Therapy (2008), 16(10):1727-1736.

Thomas et al., "Progress and Problems with the Use of Viral Vectors for Gene", Nat. Rev. Genet. (2003), 4(5):346-358.

Clark, et al.; "A future for transgenic livestock"; Nature Reviews Genetics; vol. 4, No. 10, pp. 825-833 (Oct. 2003).

Do Carmo, et al.; "Modeling Alzheimer's disease in transgenic rats"; Molecular Neurodegeneration; vol. 8, No. 37, 11 pages (2013).

(56) References Cited

OTHER PUBLICATIONS

Heymann, et al.; "Expression of Bacteriorhodopsin in Sf9 and COS-1 Cells"; Journal of Bioenergetics and Biomembranes; vol. 29, No. 1, pp. 55-59 (1997).
Ramalho, et al.; "Mouse genetic corneal disease resulting from transgenic insertional mutagenesis"; Br. J. Ophthalmol.; vol. 88, No. 3, pp. 428-432 (Mar. 2004).
Ristevski; "Making Better Transgenic Models: Conditional, Temporal, and Spatial Approaches"; Molecular Biotechnology; vol. 29, No. 2, pp. 153-163 (Feb. 2005).
Sigmund; "Viewpoint: Are Studies in Genetically Altered Mice Out of Control?"; Arterioscler Thromb Vasc. Biol.; vol. 20, No. 6, pp. 1425-1429 (Jun. 2000).
Sineshchekov et al.; "Intramolecular Proton Transfer in Channelrhodopsins"; Biophysical Journal; vol. 104, No. 4, pp. 807-807 (Feb. 2013).
Han, et al., "Millisecond-Timescale Optical Control of Neural Dynamics in the Nonhuman Primate Brain"; Neuron; vol. 62, pp. 191-198 (Apr. 30, 2009).
Han, et a.; "Virogenetic and optogenetic mechanisms to define potential therapeutic targets in psychiatric disorders"; Neuropharmacology; vol. 62, pp. 89-100 (2012).
Zhang, et al.; "Optogenetic interrogation of neural circuits: Technology for probing mammalian brain structures"; Nature Protocols; vol. 5, No. 3, pp. 439-456 (Mar. 1, 2010).
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Asano, et al.; "Optically Controlled Contraction of Photosensitive Skeletal Muscle Cells"; Biotechnology & Bioengineering; vol. 109, No. 1, pp. 199-204 (Jan. 2012).
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
Genbank Accession No. BAA09452.1; Mukohata et al.; pp. 1 (Feb. 10, 1999).
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Mueller, et al.; "Clinical Gene Therapy Using Recombinant Adeno-Associated Virus Vectors"; Gene Therapy; vol. 15, pp. 858-863 (2008).
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Day, et al.; "The Nucleus Accumbens and Pavlovian Reward Learning"; Neuroscientist; vol. 13, No. 2, pp. 148-159 (Apr. 2007).
Knopfel, et al.; "A comprehensive concept of optogenetics"; Progress in Brain Research; vol. 196, pp. 1-28 (2012).
Packer, et al.; "Targeting Neurons and Photons for Optogenetics"; Nature Neuroscience; vol. 16, No. 7, pp. 805-815 (Jul. 2013).
Duffy, et al.; "In vivo imaging of transplanted stem cells in the central nervous system"; Curr Opin Genet Dev. Oct. 2014 ; 28: 83-88. doi:10.1016/j.gde.2014.09.007.
Feng, et al.; "Optical control and study of biological processes at the single cell level in a live organism"; Rep Prog Phys. Jul. 2013 ; 76(7): 072601. doi:10.1088/0034-4885/76/7/072601.
Stroh, et al.; "Tracking Stem Cell Differentiation in the Setting of Automated Optogenetic Stimulation"; Stem Cells; vol. 29, pp. 78-88 (2011).
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Bowers, et al.; "Genetic therapy for the nervous system"; Human Molecular Genetics; vol. 20, No. 1, pp. R28-R41 (2011).
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
GenBank Accession No. AC096118.6; Rattus norvegicus clone CH230-11 B15, 1-4, 24-25, Working Draft Sequence, 3 unordered pieces. May 10, 2003.
GenBank Accession No. U79717.1; Rattus norvegicus dopamine 02 receptor 1-4, 24-25 gene, promoter region and exon 1. Jan. 31, 1997.
Haim, et al.; "Gene Therapy to the Nervous System"; Stem Cell and Gene-Based Therapy; Section 2, pp. 133-154 (2006).
Pandya, et al.; "Where in the Brain is Depression?"; Curr. Psychiatry Rep.; vol. 14, pp. 634-642 (2012).

(56) References Cited

OTHER PUBLICATIONS

Stonehouse, et al.; "Caffeine Regulates Neuronal Expression of the Dopamine 2 Receptor Gene"; Molecular Pharmacology; vol. 64, No. 6, pp. 1463-1473 (2003).
Bibel, et al.; "Differentiation of mouse embryonic stem cells into a defined neuronal lineage"; Nature Neuroscience; vol. 7, No. 9, pp. 1033-1009 (Sep. 2004).
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Nargeot et al.; Molecular basis of the diversity of calcium channels in cardiovascular tissues European Heart Journal, 1997, Supplemental A, A15-A26.
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Definition of integral. Merriam-Webster Dictionary, retrieved on Mar. 20 2017; Retrieved from the internet: <http://www.merriam-webster.com/dictionary/integral>.
Ferenczi, et al.; "Optogenetic approaches addressing extracellular modulation of neural excitability"; Scientific Reports; vol. 6, 20 pages (Apr. 5, 2016).
Li, et al.; "A Method for Activiation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Davidson, et al.; "Viral Vectors for Gene Delivery to the Nervous System"; Nature Reviews Neuroscience; vol. 4, pp. 353-364 (May 2003).
Belzung et al., "Optogenetics to study the circuits of fear- and depresssion-like behaviors: A critical analysis," Pharmacology, Biochemistry and Behavior, 2014, 122: 144-157.
Bernstein & Boyden "Optogenetic tools for analyzing the neural circuits of behavior," Trends Cogn Sci., 2011, 15(12): 592-600.
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).
Definition of Implant; Merriam-Webster Dictionary; retrieved Nov. 7, 2016 (http://www.merriam-webster.com/dictionary/implant).
Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).
Masaki, et al.; "$\beta$2-Adrenergic Receptor Regulation of the Cardiac L-Type Ca2+ Channel Coexpressed in a Fibroblast Cell Line"; Receptor; vol. 5, pp. 219-231 (1996).
Tsuchida; "Nervous Control of Micturition"; The Japanese Journal of Urology; vol. 80, No. 9, pp. 1257-1277 (1989).
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Ahmad, et al. "Heterplogous expression of bovine rhodopsin in *Drosophila* photoreceptor cells" Invest Ophthalmol Vis Sci. 2006, 3722-3728.
Clare "Targeting Ion Channels for Drug Discovery" Discov Med. 2010 vol. 9 No. 46 pp. 1-6.
Clare "Functional Expression of Ion Channels in Mammalian Systems" Protein Science Encyclopedia A.R. Fersht (Ed.) 2008 pp. 79-109.
Reeves et al., "Structure and function in rhodosin: A tetracycline-inducible system in stable mammalian cell lines for high-level expression of opsin mutants" PNAS, 2002 vol. 99 No. 21 pp. 13413-13418.
Friedman, et al.; "VTA Dopamine Neuron Bursting is Altered in an Animal Model of Depression and Corrected by Desipramine"; J. Mol. Neurosci.; vol. 34, pp. 201-209 (2008).
Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).
Weiss, et al.; "Galanin: A Significant Role in Depression?"; Annals New York Academy of Sciences; vol. 863, No. 1, pp. 364-382 (1998).
Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).

(56) References Cited

OTHER PUBLICATIONS

Smith, et al.; "Proton binding sites involved in the activation of acid-sensing ion channel ASIC2a"; Neuroscience Letters; vol. 426, pp. 12-17 (2007).

Erbguth et al. "Bimodal Activation of Different Neuron Classes with Spectrally Red-Shifted Channelrhodopsin Chimera C1V1 in Caenorhabditis elegans," PLOS One, 2012, vol. 7 No. 10, pp. e46827/1-e46827/9.

Li et al.; "Role of a Helix B Lysine Residue in the Photoactive Site in Channelrhodopsins," Biophysical Journal, 2014, vol. 106, pp. 1607-1617.

Prigge et al.: "Functional Studies of Volvox Channelrhodopsin Chimeras," Biophysical Journal, 2010, vol. 98, No. 3, Suppl. 1, 3694 Poster, 1 page.

Prigge et al.; Color-tuned Channelrhodopsins for Multiwavelength Optogenetics, J. Biol. Chem. 2012, vol. 287, No. 38, pp. 31804-31812.

Tsunoda & Hegemann "Glu 87 of Channelrhodopsin-1 Causes pH-dependent Color Tuning and Fast Photocurrent Inactivation," Photochemistry and Photobiology, 2009, vol. 85, No. 2, pp. 564-569.

Coleman, et al.; "Assessing Anxiety in Nonhuman Primates"; Ilar Journal; vol. 55, No. 2, pp. 333-346 (2014).

Maestripieri, et al.; "A modest proposal: displacement activities as an indicator of emotions in primates"; Anim. Behav.; vol. 44, pp. 967-979 (1992).

Jones, et al.; "Animal Models of Schizophrenia"; British Journal of Pharmacology; vol. 164, pp. 1162-1194 (2011).

Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).

Sofuoglu, et al.; "Cholinergic Functioning in Stimulant Addiction: Implications for Medications Development"; CNS Drugs; vol. 23, No. 11, pp. 939-952 (Nov. 1, 2009).

Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).

Boyden, et al.; "A history of optogenetics: the development of tools for controlling brain circuits with light"; F1000 Biology Reports; vol. 3, No. 11, 12 pages (May 3, 2011).

Knox, et al.; "Heterologous Expression of Limulus Rhodopsin"; The Journal of Biological Chemistry; vol. 278, No. 42, pp. 40493-40502 (Oct. 17, 2003).

Lin, et al.; "Characterization of Engineered Channelrhodopsin Variants with Improved Properties and Kinetics"; Biophysical Journal; vol. 96, No. 5, pp. 1803-1814 (Mar. 2009).

Daniel, et al.; "Stress Modulation of Opposing Circuits in the Bed Nucleus of the Stria Terminalis"; Neuropsychopharmacology Reviews; vol. 41, pp. 103-125 (2016).

Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).

Knopfel, et al.; "Remote control of cells"; Nature Nanotechnology; vol. 5, pp. 560-561 (Aug. 2010).

Steimer; "The biology of fear- and anxiety-related behaviors"; Dialogues in Clinical Neuroscience; vol. 4, No. 3, pp. 231-249 (Sep. 2002).

Stuber; "Dissecting the neural circuitry of addiction and psychiatric disease with optogenetics"; Neuropsychopharmacology; vol. 35, No. 1, pp. 341-342 (2010).

Lin, et al.; "Study of the Circuitry of Nucleus Accumbens and its Effect on Addiction by Optogenetic Methods: 964"; Neurosurgery; vol. 67, No. 2, p. 557 (Aug. 2010).

Duvarci, et al "The bed Nucleus of the Stria Terminalis Mediates inter-individual variations in anxiety and fear", J. Neurosci., 29(33) 10357-10361 (2009).

Matsuda "Bed nucleus of stria terminalis (BNST)" Benshi Seishin Igaku (Molecular Psychiatric Medicine), 2009, vol. 9 No. 3, p. 46-49.

Neuropsychopharmacology, 2011, vol. 36 No. Suppl.1, p. S110 (Abstract No. 67).

Neuropsychopharmacology, 2012, vol. 38 No. Suppl.1, p. S48 (Abstract No. 37.2).

Walker et al. "Selective Participation of the Bed Nucleus of the Stria Terminalis and CRF in Sustained Anxiety-like versus Phasic Fear-Like Responses," Prog Neuropsychopharmacol Bio Psychiatry, 13: 33(8) 1291-1308 (2009).

\* cited by examiner

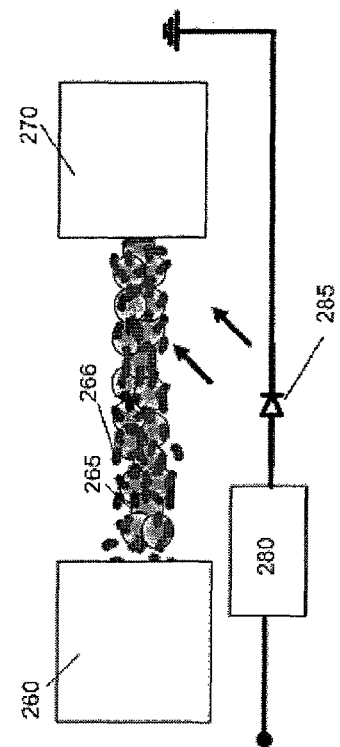
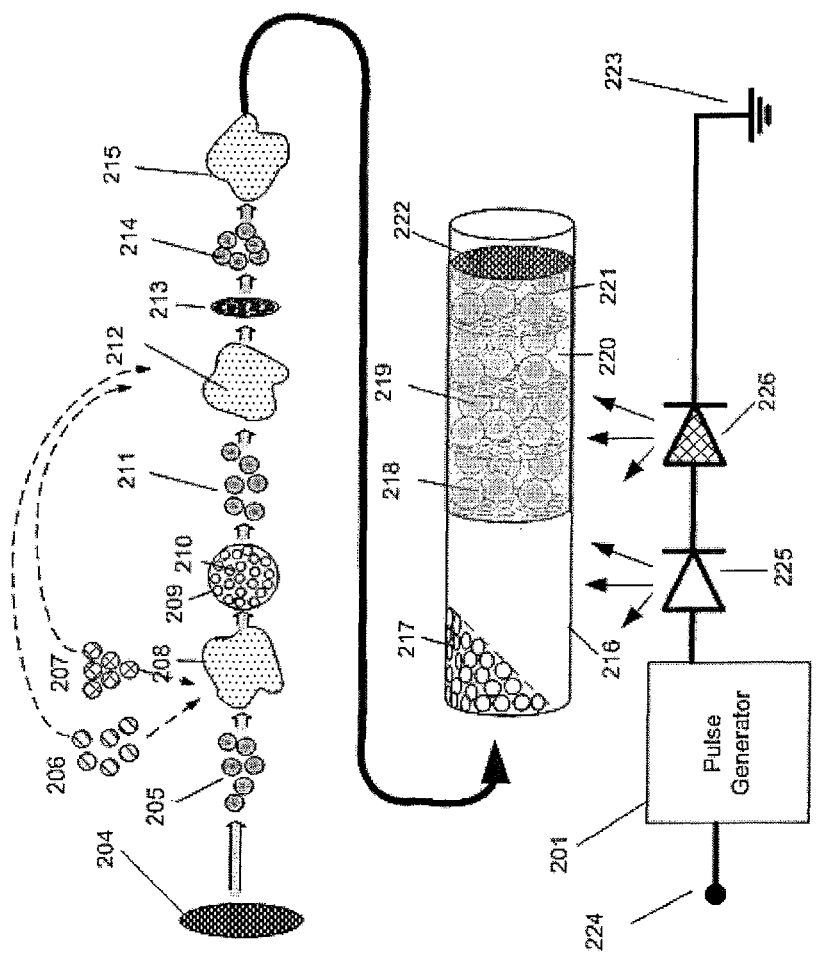
FIGURE 2A
FIGURE 2B a b

APPARATUS AND METHODS FOR CONTROLLING CELLULAR DEVELOPMENT

RELATED PATENT DOCUMENTS

This patent document is the national stage filing under 35 U.S.C. § 371 of International Application No. PCT/US2009/047701 filed on Jun. 17, 2009, which claims the benefit, under 35 U.S.C. § 119(e), of U.S. Provisional Patent Application Ser. No. 61/132,163 filed on Jun. 17, 2008 and entitled "Control of Cellular Interactions In Engineered Tissue," and of U.S. Provisional Patent Application Ser. No. 61/093,086 filed on Aug. 29, 2008, and entitled "Arrangements, Methods and Compositions Involving Modulation of Embryonic Stem Cell Differentiation with Automated Temporally Precise Optogenetic Stimulation;" this international application, and the underlying provisional applications and respective Appendic(es) are fully incorporated herein by reference. This patent document also relates to, and fully incorporates by reference, the following underlying patent documents: U.S. patent application Ser. No. 11/459,636 filed on Jul. 24, 2006 (STFD.169PA), PCT Patent Application Serial No. PCT/US2008/050628 filed on Jan. 9, 2008 (STFD.150PCT), and U.S. patent application Ser. No. 12/187,927 filed on Aug. 7, 2008 (STFD.167PA) (e.g., discussion in connection with FIGS. 1-5).

FIELD OF THE INVENTION

The present invention relates generally to methods, devices and systems for the growth and development of cells and/or tissue.

BACKGROUND

Naturally developing tissue is intrinsically of a multi-cell-type nature. A substantial portion of cultured stem cells that are implanted, die without reaching maturity or integrating themselves into a functional tissue system. The odds of survival and functional integration increase when cultured cells are allowed to develop along side of their natural companion cells. In many cases, the number of surviving cells may be improved by growing glial cells and endothelial cells or fibroblasts along with neurons. This generally holds true both in culture, and after implantation.

Tissue culture, involving the growth of tissues and/or cells separate from the organism, is typically facilitated by use of a liquid, semi-solid, or solid growth media, such as broth or agar. When intended for implantation as a solid organ, e.g., in the context of regenerative medicine, a suitable matrix is usually required. Even with the appropriate immature cells (e.g., stem cells) in place, development into function, and/or implantable tissue does not occur spontaneously. In the specific case of neural tissue, for example, brain, axonal and dendritic sprouting is shaped by activity of the various cells in the milieu. In this way, local cellular environments are crucial in the regulation of neurogenesis. Empirically, scientists have evidenced that hippocampal cell co-culture promotes hippocampal neurogenesis, and that adult NPCs grown in an environment non-permissive for neurogenesis are unable to respond to excitation. These cells communicate with one another, e.g., via chemical, molecular and electrical signals. Frequently, chemical or molecular signaling is triggered by electrical signaling; for example an endocrine cell releasing a growth factor when electrically stimulated. Activity-dependent competition frequently occurs in this context. For example, more active neurons from one brain region may overgrow regions occupied by less active neurons. Conversely, limiting activity in a brain region during development results in functional deficits. Electrical signaling and molecular signaling are the most common approaches by which cells in culture control mutual behavior within the milieu.

Electrical signaling is an important part of nerve cell development and for many other types of cells including endocrine cells and muscle cells. The application of electrical pulses to neuronal progenitor cells (NPCs) causes them to evolve from generic sphere-like structures into mature neurons, sprouting axons and dendrites along the way, and establishing electrical connections with other neurons.

Chemical/molecular signaling is frequently triggered by electrical signaling. For example, adult neurogenesis and maturation of NPCs is greatly enhanced by excitatory stimuli and involves Cav1.2/1.3 channels and NMDA receptors. These $Ca^{2+}$ influx pathways are located on the proliferating NPCs, allowing them to directly sense and process excitatory stimuli. The $Ca^{2+}$ signal in NPCs leads to rapid induction of a gene expression pattern that facilitated neural development. This leads to synaptic incorporation of new neurons into active neural circuits. Another example is endocrine cell releasing a growth factor when electrically stimulated, but may also be triggered by other molecular or chemical signals. Nerve growth factor (NGF) is secreted by cells surrounding a developing neuron, such as glial cells, and is critical to the development and long-term survival of neurons. Nerve growth factor (NGF), is a small protein secreted by glial cells as well as by some neurons, and induces the differentiation and survival of target neurons. NGF binds to and activates its high affinity receptor (TrkA), and a low-affinity receptor (LNGFR), and promotes neuron survival and differentiation. Conversely, molecular modifications of NGF such as proNGF can elicit apoptosis. Brain-derived neurotrophic factor (BDNF) is released from cells including fibroblasts and endothelial cells (such as those within capillaries), and serves to promote growth and development of neurons, including axonal and dentdritic sprouting. Deficient expression of BDNF not only impairs the development of neurons, but also impairs the development of capillaries and the survival of endothelial cells themselves. NGF, BDNF and neurotrophin-3 bind to the neurons bearing tyrosine kinase (trk) receptors trk A, trk B and trk C. Vascular endothelial growth factor (VEGF)-D is a member of the VEGF family of angiogenic growth factors that recognizes and activates the vascular endothelial growth factor receptor (VEGFR)-2 and VEGFR-3 on blood and/or lymphatic vessels. Neuropilin-1 (NRP-1), for example, is one of the vascular permeability factor/vascular endothelial growth factor (VPF/VEGF) receptors that is involved in normal vascular development.

Electrical and chemical/molecular signaling has limitations, however. For example, electrical stimulation is rather agnostic to the types of cells that it activates. In brief, an electric field of a given distribution displays relatively low preference with respect to the type of cells which they affect. Electrodes indiscriminately influence the behavior of activate neurons, glia, endocrine cells, muscle cells, and even the growth of bone within the stimulated area. As a result, physical proximity of an electrode pole to a given cell may be the single largest determining factor as to whether or not it is affected. Because of these limitations, it is generally not possible to exclusively affect a specific class of cell in heterogeneously populated tissue.

Intercellular molecular signaling, although frequently cell-type specific, is often not readily modified artificially in a physically tightly knit cell culture environment, which frequently resists permeation of required growth factors, particularly in the absence of efficient capillary development. Proper and/or ideal distribution of chemical and molecular signaling agents including K+, BDNF, NGF, and VEGF may be best achieved using the cells that natively produce these agents, in their natural spatial configurations with respect to the target cells. Because molecular signaling is frequently triggered by electric signals to the source cell, such signaling is subject to the non-specify of electrical activity within the milieu.

There are a number of challenges to successful production of a cultured neuronal tract using stem cells (either adult stem cells or embryonic stem cells). These challenges have included issues emanating from maturing stem cell arrays remaining in evolution continuously, and connections being made between them early in their life where the connections may or may not be maintained as they develop further. Some method of ongoing functional reinforcement, either natural or artificial, is likely necessary for the long term viability of a cultured tract.

Efforts continue toward the goal of facilitating the consistent sprouting and growth of dendrites and axons in a predictable direction, as present studies show their natural development tendency to be lateral and/or randomly-directed growth.

SUMMARY

The present invention is exemplified in a number of implementations and applications, some of which are summarized below.

In certain regards, the present invention is directed to providing mechanisms and methodology for individually and separately controlling the activity of specific cell types within a mixed tissue culture milieu, in order to direct optimal development of that tissue.

Certain aspects of the present invention are directed to using the intrinsic properties of axons and dendrites to facilitate the controlled development of young neurons. As specific examples, dendrites and axons have different associated chemo-attractants, temporal properties (axons grow faster than dendrites), and physical dimensions (axons are longer and thinner than dendrites). These properties may provide means by which one shape the development of young neurons.

According to one example embodiment, a method for facilitating cellular interactions in biological tissue or cell culture provides controllable activation of a selected type of stem cell among a plurality of cell types. The method includes introducing a microbial opsin into a region of the tissue or cell culture that includes a selected type of stem cell, by expressing the microbial opsin in the stem cell. A light source is then introduced near the stem cell, and the light source is used to controllably activate the light to direct pulses of illumination from the light source to the selected type of stem cell, for selectively controlling the growth and development of the stem cell in a manner that is independent of the growth and development of the other types of cells.

Also consistent with the present invention, one specific embodiment is directed to providing for discrete communication with specific cell types within a mixed-cell culture milieu, whereby cells of individual types and individual roles in tissue development can be governed. Each of these selected cell types can thereby be induced to release their specific products on demand, as determined manually, or by a computer system. This approach is intended to enable maximal control of virtually all aspects of a tissue being cultured or engineered.

Another specific embodiment provides for artificially growth of a tissue within a predetermined spatial and geometric configuration. For example, a longitudinally-extending system of electrically interconnected neurons which propagates signals detected at one end of the system, and outputs a corresponding signal at the other end. An artificially-produced neuronal tract could serve as a replacement for a damaged neuronal tract, for example in an injured human brain or spinal cord.

Another specific embodiment is directed to a method for internal pacing of portion of a brain, e.g., hypoactive or hyperactive portion of a brain being internally paced, while using another portion of the brain as the controller (e.g., as opposed to an external source like a DBS pulse generator).

Yet another specific embodiment is directed to retaining stem cell somas enclosed within a predetermined range of migration. This aspect of the present invention recognizes that stem cells can escape from their implanted location, particularly embryonic stem cells, and therefore may seed themselves as cancerous tumors within the body.

Applications include the culturing of tissue, and the continued nurturing stimulation applied to an area of cells implanted in vivo. The specification details the application of an optogentic approach which endows specific targeted cell types with a privileged channel of communication. Non-targeted cell types remain unaffected by that particular wavelength of light, but may be sensitized to a different wavelength or signal. Embodiments consistent therewith specifically regard the regulation of neural tissue development suited for spinal cord or brain injury repair. However the same general principles of independent control of different cell types within the developing tissue apply to heart, liver, pancreas, kidney, bone and other tissues of the body, in culture or implanted in vivo.

Another aspect of the patent invention is directed to use and introduction of a microbial opsin into embryonic stem cells and the development of optogenetic technology for stem cell engineering applications, with a novel automated system for noninvasive modulation of embryonic stem cell differentiation employing fast optics and optogenetic control of ion flux.

According to yet another embodiment, the present invention is directed to CNS (central nervous system) disease/behavior treatment (applicable, e.g., to Parkinson's Disease, stroke, and spinal cord injury) by functionalizing neurons to integrate into the host after intracerebral transplantation. To this end, the present invention is directed to stem cell therapy for CNS disease/behavior treatment wherein differentiated cells are generated, integrated into native neural circuitry and then controlled selectively by light.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which:

FIGS. 2a and 2b illustrate an assembly of biological and synthetic components, and stimulation means for multichannel stimulation tissue culture, according to an embodiment of the present invention;

Figure 1:
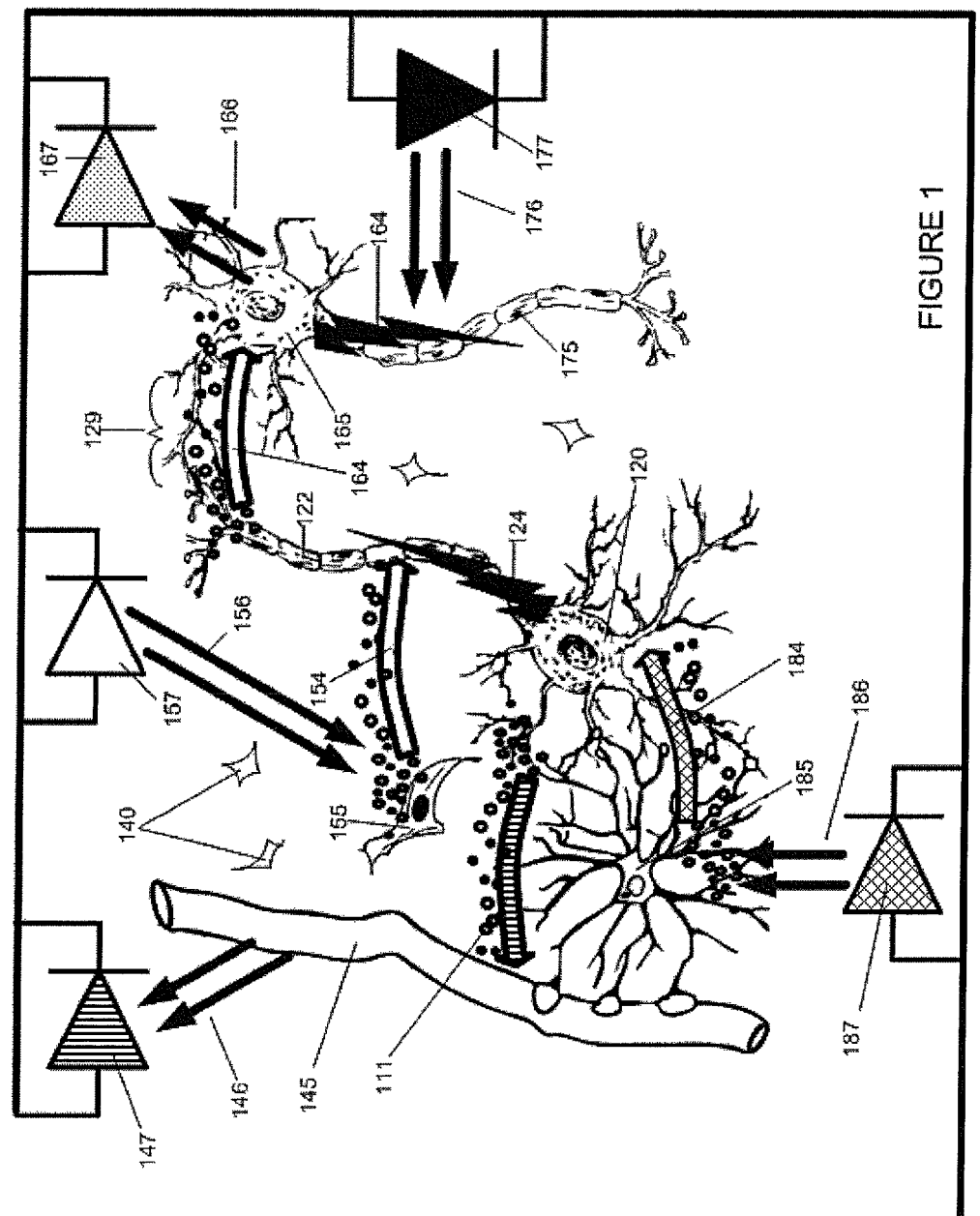
FIG. 1 illustrates a system, according to an embodiment of the present invention, involving classes of cell types that function in a coordinated fashion during tissue growth, development, activity and maintenance, for selective activation (e.g., stimulation or suppression), and their detection of their activity.
Figure 1:
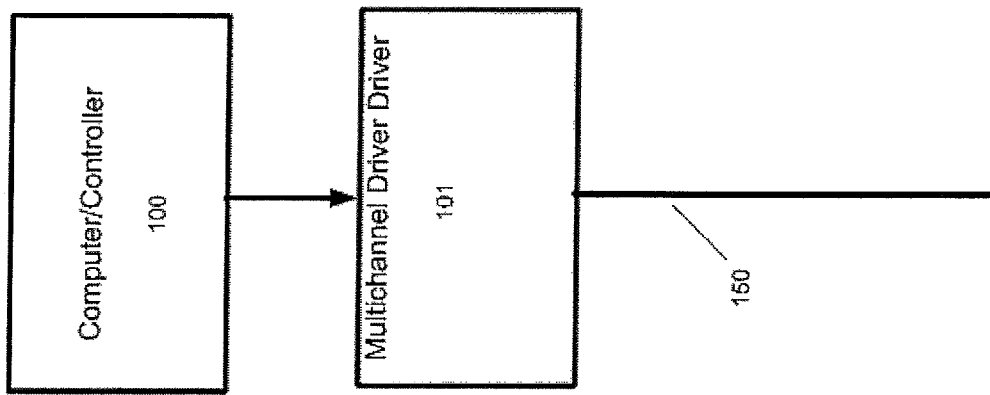

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is directed to methods and apparatus for culturing and promoting the growth of stem cells, such as embryonic stem cells, in biological tissue. The present invention has been found to be particularly suited for use in arrangements and methods dealing with growth of stem cells in neural networks. While the invention is not necessarily limited to such biological environments, various aspects of the invention may be appreciated through a discussion of various examples using this context.

Consistent with one example embodiment of the present invention, a method for facilitating cellular interactions in biological tissue or cell culture provides controllable activation of a selected type of stem cell among a plurality of cell types whether or not present in the tissue or cell culture. The method includes introducing a microbial opsin into a region of the tissue or cell culture that includes a selected type of stem cell, by expressing the microbial opsin in the stem cell. A light source is then introduced near the stem cell, and the light source is used to controllably activate the light to direct pulses of illumination from the light source to the selected type of stem cell, for selectively controlling the growth and development of the stem cell in a manner that is independent of the growth and development of the other types of cells.

FIG. 1 illustrates several classes of cell types which function in a coordinated fashion during tissue growth, development, activity and maintenance. These cell types may be selectively stimulated or suppressed, and their activity may be detected, for example by the array of colored LEDs and selective-color-filtered photodiodes. Each LED and photodiode are controlled by separate channels coupled to a computer. Computer controller 100 sends and receives inputs and outputs via multichannel driver 101, which in turn, communicates with each cell via transducers (LEDs 187, 177 and 156, and photodiodes 167 and 147), connected via multichannel cable 150. LED 187 emits light 186 which produces ion channel modulation in glial cell 185 via ChR2. This produces a release of neurotrophic chemicals 184 (for example BDNF), which are received by neuron 120, thereby inducing growth and development in neuron 120. Neuron 120, as a product of its growth, releases tropic chemicals such as vascular-endothelial growth factor (VEGF), which is received by capillary 145, and promotes growth of the network of which capillary 145 is a part. LED 177 emits light 176 which produces ion channel modulation in neuron 175. Band-filtered photodiode 167 receives light 166 of the wavelength emitted by an indicator (such as voltage dye) released from neuron 165 in response to action potential 164. LED 157 emits light 156 of a wavelength which produces ion channel modulation in fibroblast 155. Band-filtered photodiode 147 receives light 146 of the wavelength emitted by an indicator for example those characteristic wavelengths emitted, for example, by Fura-2 or RH1691. Neuron 120 has axon 122, which communicates via synapse 129 with second neuron 165 with axon 175. Neurons 120 receive metabolic support from glial cell 185. Glia cell 185 draws nutrition from end-feet 186 on capillary 145, and delivers nutrition to neuron cell 120 via end-feet 187. Microglia 140 (representative sample shown) are dispersed throughout. $Ca^{2+}$ influx pathways are located on the proliferating NPCs, allowing them to directly sense and process excitatory stimuli. The Ca2+ signal in NPCs leads to rapid induction of a gene expression pattern that facilitated neural development. This leads to synaptic incorporation of new neurons into active neural circuits. Another example is endocrine cell releasing a growth factor when electrically stimulated, but may also be triggered by other molecular or chemical signals. Nerve growth factor (NGF) is secreted by cells surrounding a developing neuron, such as glial cells, and is critical to the development and long-term survival of neurons. Nerve growth factor (NGF) is a small protein secreted by glial cells as well as by some neurons, and induces the differentiation and survival of target neurons. NGF binds to and activates its high affinity receptor (TrkA), and a low-affinity receptor (LNGFR), and promotes neuron survival and differentiation. Conversely, molecular modifications of NGF such as proNGF can elicit apoptosis. Brain-derived neurotrophic factor (BDNF) is released from cells including fibroblasts and endothelial cells (such as those within capillaries), and serves to promote growth and development of neurons, including axonal and dentdritic sprouting. Deficient expression of BDNF not only impairs the development of neurons, but also impairs the development of capillaries and the survival of endothelial cells themselves. NGF, BDNF and neurotrophin-3 bind to the neurons bearing tyrosine kinase (trk) receptors trk A, trk B and trk C. Vascular endothelial growth factor (VEGF)-D is a member of the VEGF family of angiogenic growth factors that recognizes and activates the vascular endothelial growth factor receptor (VEGFR)-2 and VEGFR-3 on blood and/or lymphatic vessels. Neuropilin-1 (NRP-1, for example, is one of the vascular permeability factor/vascular endothelial growth factor (VPF/VEGF) receptors that is involved in normal vascular development. Optogentic methods may be used to trigger the release of compounds such as BDNF, NGF, GDNF and VEGF.

One function of G-Proteins is to mediate the process by which a stimulus upon a cell impacts the response of that cell; for example, the timing of electrical spikes delivered upon a neuron may or may not translate into the emergence of excitatory postsynaptic potentials, depending upon G-protein activities. G-proteins may carry out their roles by using various subordinate mediators. G-proteins such as Gx and Gq may be induced (by optical or pharmacological stimulation) so as to release factors such as BDNF, NGF, GDNF and VEGF. Stimulation of the G-protein may be accomplished in a cell-type-specific manner (for example using cell-type-specific genetic targeting and optogenetic stimulation methods as described in one or more of the underlying provisional patent documents and as described in Airan R. D., Thompson K. R., Fenno L. E., Bernstein H., Deisseroth K., *Temporally Precise in vivo Control of Intracellular Signaling*, Nature, 2009 Apr. 23, 458(7241):1025-9, Epub 2009 Mar. 18. When this is done, the regulation and control of a cell's response level to such factors applies only to the selected type of cell, and not to other adjacent populations within a tissue culture, neural circuit, animal, or patient. G-proteins may also be used to control the release of dopamine, norepinephrine, serotonin, vasopressin, oxytocin, and other neurotransmitters and hormones. Control of G-protein activity, thereby permit control of cellular differentiation, and which neural circuits are turned on or off at a given time.

Methods for external readout of levels of cellular activity within a network are known in the art. As described in Knopfel et al., *Optical probing of neuronal circuit dynamics: genetically encoded versus classical fluorescent sensors*, Trends Neurosci. 2006 Mar. 29, 3:160-6, such methods include use of non-protein calcium sensors such as Fura-2, Oregon green 488 BAPTA-1, and X-Rhod-5F; genetically-encoded calcium sensors, such as yellow cameleon 3.6, G-CaMP2, Camgaroo-2 and TN-L15; non protein voltage sensors such as di-4-ANEPPS and JPW3028; and hybrid voltage sensors such as hVOS, genetically-encoded sensors such as FlaSh, SPARC and VSFP1. Additionally, absorbance-based measures of calcium flux such as RH-155 may be used by means known in the art.

Methods of providing readout regarding expression of cell products and the subpopulations of cells that produce them with an antibody linked to a fluorescent dye. For example, for gauging developmental stage of cellular development, one may use nestin staining (see, e.g., underlying U.S. provisional application No. 61/093,086).

Additionally, both size and morphology degree of differentiation in developing cells may be assessed and read out using automated image analysis software and systems. One example is a microscopy system built upon the PERL-based OME server project at Open Microscopy Environment (www.openmicroscopy.org), which implements image-based analysis of cellular dynamics and image-based screening of cellular localization or phenotypes. Another example of software readout may be based upon BD IPLab Advanced Image Analysis Software (BD Biosciences, Rockville, Md.). Other methods of providing readout regarding cellular activity are known in the art, and include spectroscopy (absorbance and transmittance), functional magnetic resonance imaging (such as use of the BOLD effect), and positron emission tomography. Readout on cellular metabolic activity may also be obtained via electronic chemical "sniffers" which react to the presence of gasses such as carbon dioxide.

FIG. 2a illustrates an assembly of biological and synthetic components, and stimulation means for multichannel stimulation tissue culture within an engineered tissue culture matrix. Pulse generator 201 provides power to LED 225 and LED 226, each of which emit a different spectrum and parameters, while power 224 and ground 223 provide the current flow required. LED 225 may, for example, emit blue light at 50 Hz, while LED 226 emits yellow light at 100 Hz. The electronics described in FIG. 1 are simplified for illustrative purposes. In practice, multiple pulse generators operating separately are used for the implementation of separate channels, and these channels may be activated independently depending upon readout data entering the system, as will be described in subsequent figures. Neuronal progenitor cells (NPCs, neural stem cells) 205, glial progenitor cells (GPCs, glial stem cells) 206 and vascular progenitor cells (VPCs, vascular stem cells) 207 are added to cellular growth media 208. All are held within encapsulating porous membrane 217, and against porous membrane 210, enclosed by the addition of porous membrane 204. Porous barrier membrane 209 containing membrane pores 210 serves to prevent cell migration out of the engineered matrix, and prevents clumping in other portions of the engineered matrix. Porous membrane 209 may be composed of materials such as polyethylene terephthalate porous membrane. Generally, pores 210 are of a diameter between approximately 3 and 7μ. At these dimensions, pores 10 are generally too small for stem cell bodies (soma) to pass through, but large enough for dendrites and axons to pass through. Porous membrane 209 serves as an anchoring layer (either above, below, above and below or enclosing around) which restricts cell migration before and during the growth of axons and dendrites, and provides easy means for removal of the cells from the culturing apparatus prior to implantation. In an adjacent but separated compartment of the engineered matrix, NPCs 211 are added to cellular growth media 212, and more glial precursor cells and vascular precursor cells 207 may be added. Porous barrier membrane 213 serves to close off this compartment of the matrix to prevent migration or clumping, as was previously done with porous membrane 210. In a subsequent compartment, NPCs 214 are again added to cellular growth media 215, and the additional cell types previously specified. Encapsulating porous membrane 216 containing membrane pores 217 encloses the entire engineered matrix described. Encapsulating porous membrane 216 may be composed of materials such as polyethylene terephthalate porous membrane. Generally, pores 217 are of a diameter between approximately 3 and 7μ. At these dimensions, pores 217 are generally too small for stem cell bodies (soma) to pass through, but large enough for dendrites and axons to pass through. These pores 217 also permit physiological gas exchange, and the influx of nutrients from microvascular structures and glial cells located outside of luminous membrane 216. Cell and media compartment 218, 219, 220, 221 are analogous to the compartmentalized cell groups described above, and likewise serve to prevent migration or clumping.

Under specific conditions known in the art, a variety of cells of various lineages may be induced to produce any of a variety of products or growth factors. For example, neurons themselves may secrete BDNF, as well as gastric hormones (such as vaso-intestinal peptide (VIP) or somatastatin), much like endodermally-derived cells normally do. In an alternative embodiment, neural stem cells or pluripotent stem cells or induced pluripotent stem cells (iPS) (Takahahi et al., Yu et al.) may be used in place of more differentiated counterparts, with some portions acquiring, for example, a neuronal path of development, and others assuming, for example, a vascular path of development.

FIG. 2B illustrates in a generic manner, how two portions of the brain or body, region 260 and region 270, respectively, may be functionally connected or re-connected using cells or tissues grown in accordance with the present invention. In the case of the brain, regions 260 and 270 may represent two brain nuclei, the natural connection between which has been severed, for example by a cerebrovascular accident. In the case of a spinal cord injury, regions 260 and 270 may represent the brain and a formerly paralyzed muscle, respectively. In the case of peripheral nerves, 260 and 270 may represent a spinal cord ganglion and a deafferentated hand, respectively. In the case of a cardiomyopathy, regions 260 and 270 may represent the vagus nerve and newly regenerated heart tissue, respectively. Cells 265 may be neural, glial, and vasculor cells or precursor (stem) cells, and are held in place by artificial matrix material 266, such as a porous polyethylene terephthalate film. Pulse generator 280 provides power to LED 285 to produce light emissions which fall upon cells 265.

Figure 3B:
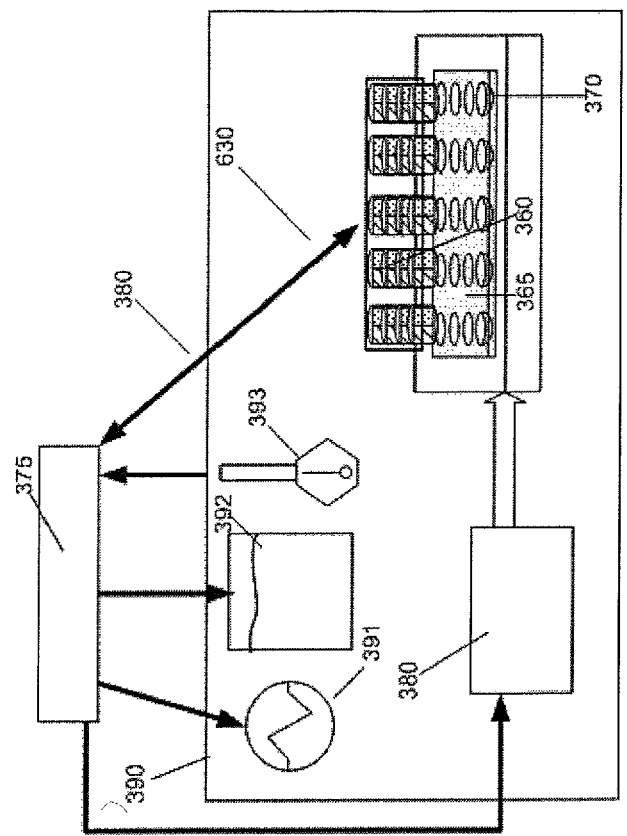
FIGS. 3a and 3b illustrate a system for culturing tissue samples in accordance with the present invention.
Figure 3A:
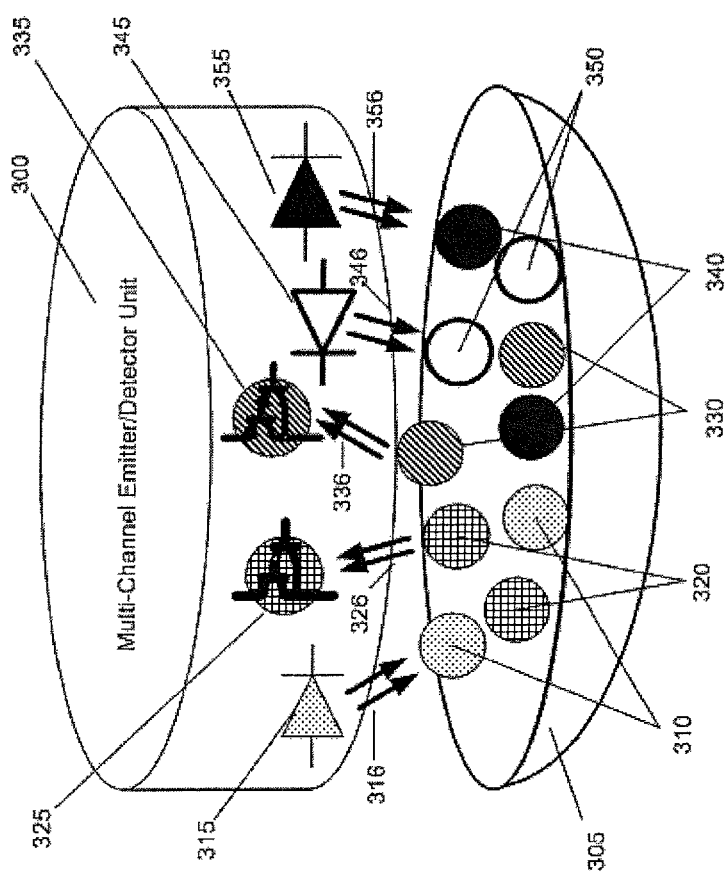

Also in accordance with the present invention, FIGS. 3a and 3b show a system for efficiently culturing numerous tissue samples. In a more particular implementations thereof, the system of FIG. 3a is a high-throughput multi-wall system for efficiently culturing numerous tissue samples in parallel. FIG. 3a shows a multichannel emitter-detector unit as suited to the present invention. Multichannel emitter-detector unit 300 includes LED 315, phototransistor 325, phototransistor 335, LED 346 and LED 356, and is placed over tissue culture well 305, containing cells 310, 320, 330, 340 and 350. LED 315 emits a specific wavelength band of light 316 which is received by type-X cells 310. LED 345 emits a specific wavelength band of light 346 which is received by type-Y cells 350. LED 355 emits a specific wavelength band of light 356 which is received by type-Z cells 340. Phototransistor 325 receives a specific wavelength band of light 326 which is emitted by type V cells 320. Phototransistor 335 receives a specific wavelength band of light 336 which is emitted by type-W cells 330. In one embodiment, cell type V may be a neuron, cell type W may be an astrocyte, cell type X may be an astrocyte, cell type Y may be a fibroblast, and cell type Z may be a pancreatic beta cell. Cell types are referenced with variables V, W, X, Y, Z, in order to emphasize the diversity of cell types that are amenable to this method of control. Furthermore, any of these variable may be of the same type as that represented by another variable. For example, a type V cell could be identical to a type X cell.

FIG. 3b show a high-throughput multiwall incubation control system for efficiently culturing numerous tissue samples in parallel in accordance with the present invention. In FIG. 3A, environmental control chamber 390 contains culture plate actuators 380, and culture plates 365, each containing tissue culture wells 370 (representative example). Multichannel emitter/detector unit 360 (representative example) is analogous with multichannel emitter/detector unit 300 of FIG. 3a, and is arranged into arrays of emitter/detector units 360, each of which is controlled by computer 375. Each multichannel emitter/detector units 360 sends stimuli and receives readouts including feedback from the stimuli, from the developing tissue in wells 370. Stimulation instructions and readout values are sent and received, respectively, by computer 375. Appropriate environmental conditions are maintained by heater 391, humidifier/gas mixture control 392, and thermostat 393, as coordinated by computer 375.

Figure 4:
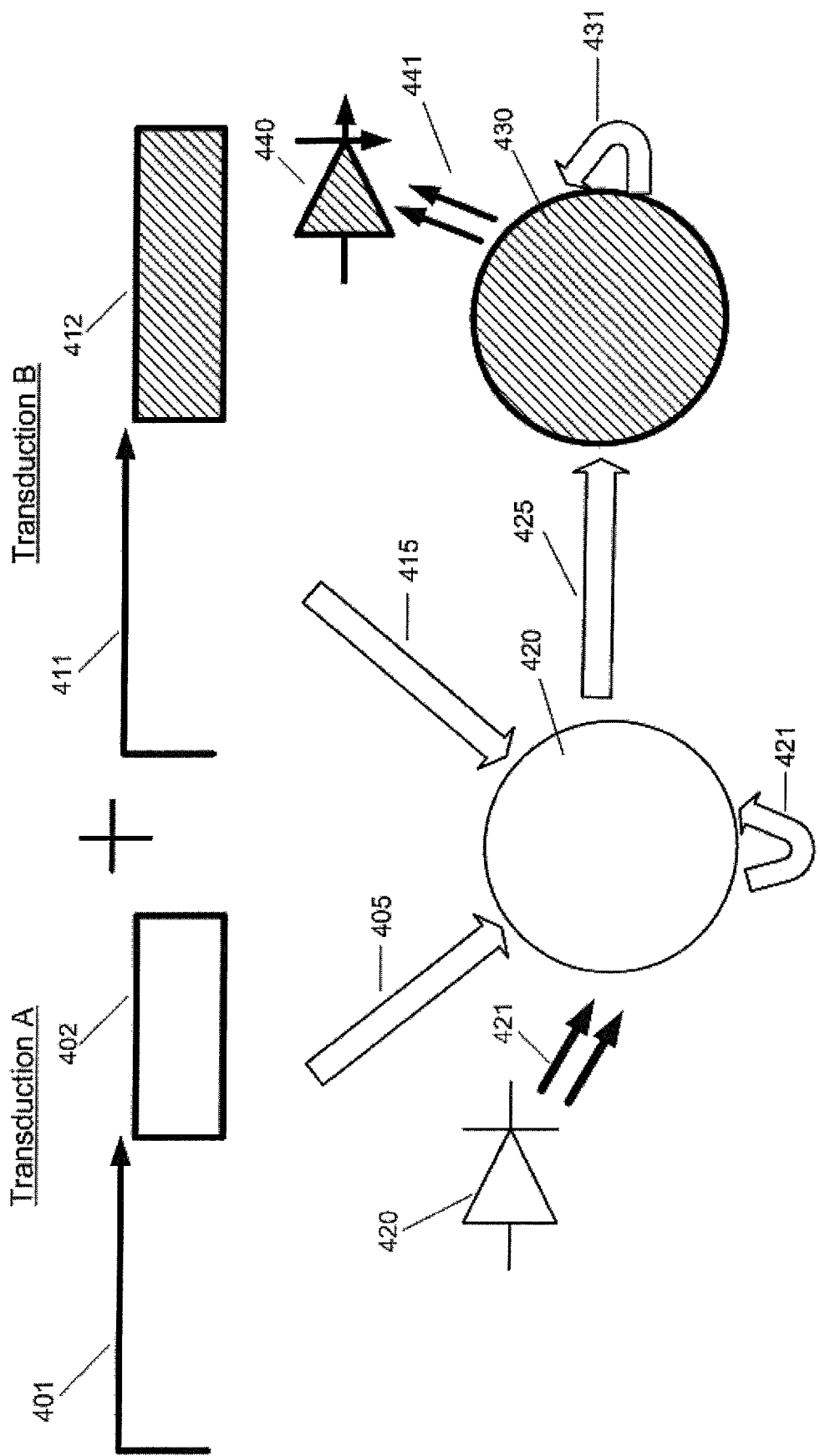
FIG. 4 illustrates a system, also in accordance with the present invention, that uses multiple transductions used upon a cell, and shows activity feedback mediated by the activity of a secondarily impacted second cell type.

FIG. 4 illustrates the use of multiple transductions used upon a cell, and shows activity feedback mediated by the activity of a secondarily impacted second cell type. Gene 402 imparts light-sensitivity upon a host cell, for example the manner in which ChR2 creates light sensitivity in neurons. Gene 412 causes cells to give off light when they undergo a given physiological process. For example, the florescent agents described in Knopfel et al. 2006, causes neurons to give off light when they depolarize. Other examples might include a substance that effervesces light when it receives a given hormone (e.g., BDNF) or neurotransmitter, or alternatively, gives off light when it secretes a given substance, such as VEGF. Gene promoter 401 acts to promote gene 402, and gene promoter 411 acts to promote gene 412. As a result 405 of this promotion, cell 420 physiologically responds to light of wavelength band 421 which is emitted from LED 420 as determined by electronic control signals detailed in FIG. 3. The response to this light may include self-recognized responses 421 (for example enhanced axonal and dendritic development), and externally recognizable responses (425), for example the release of vascular-endothelial growth factor (VEGF), or the promotion of axonal and dendritic development in an adjacent developing nerve cell. Externally recognized response 425 is shown received by cell 430, which, in turn, produces self-recognizable responses 431 as well as light of wavelength band 441. This light emission, of course, is another form of externally recognizable response. Light of wavelength band 441 is received by photodiode 440, producing an electronic detection signal, as detailed in the description of FIG. 3.

Figure 5:
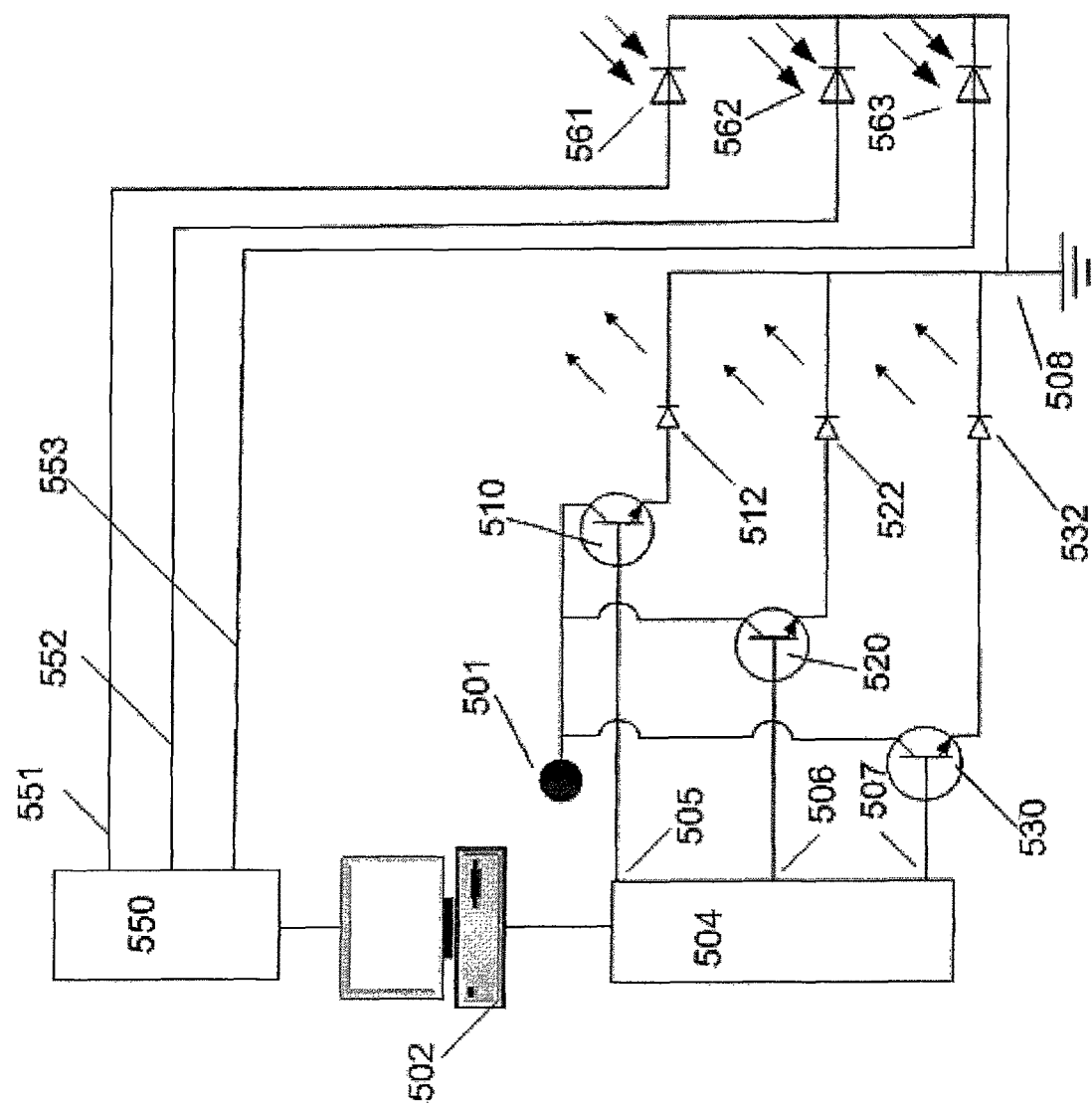
FIG. 5 illustrates a multichannel stimulation and monitoring system, also in accordance with the present invention, suitable for governing tissue development either in culture or post-implantation.

FIG. 5 illustrates a multichannel stimulation and monitoring system, suitable for governing tissue development either in culture or in-vivo/post-implantation. The principal subunits are multichannel pulse output generator 504 and multichannel detection signal receiver 550 as controlled by computer 502. Multichannel pulse output generator 504 selectively sends signals to the output portion of the apparatus. When signals are pulsed from Channel 1 Output 505, through Channel 1 switching transistor 510, power 501 is conferred to channel 1 LED 512. Likewise, when signals are pulsed from Channel 2 Output 506 through channel 2 switching transistor 522, channel 2 LED 522 is illuminated. Likewise, when signals are pulsed from channel 3 Output 507 through channel 3 switching transistor 530, channel 3 LED 532 is illuminated. Multichannel detection signal input 550 receives signals from sensors which monitor area of tissue culture or implantation. Channel 4 Input 551 receives signals from channel 4 photodiode 561 when the latter is activated. Similarly, channel 5 Input 552 receives signals from channel 5 photodiode 562 when the latter is activated. Likewise, channel 6 Input 553 receives signals from Channel 6 photodiode 563 when the latter is activated. The above circuitry operates between power 501 and ground 508. Computer 502 contains a knowledge base, algorithms or protocols for sending stimulation signals through pulse output generator 504 and for modifying these signals in accordance with patterns of signals received by multichannel signal detection receiver 550.

Figure 6:
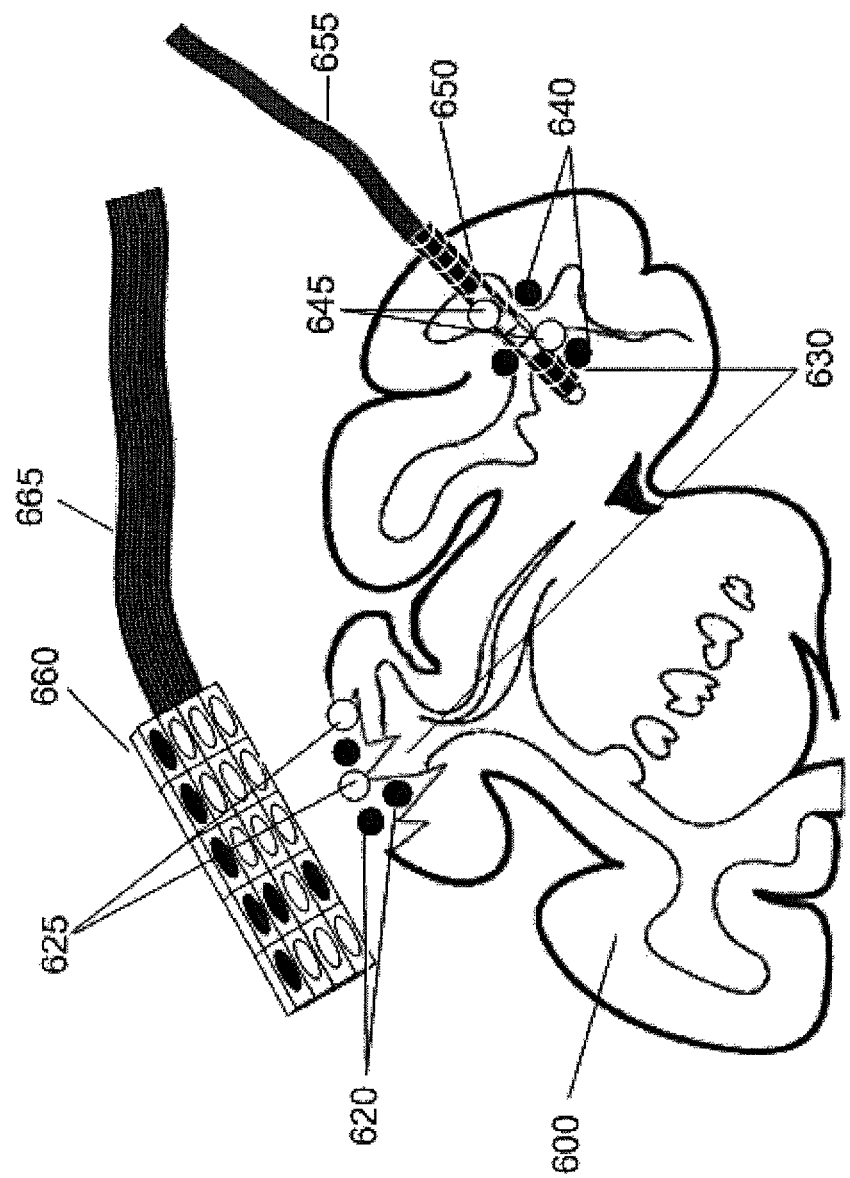
FIG. 6 is a schematic illustration of in vivo implantation and integration of cultured tissue into a living organism whereby development may be facilitated in accordance with the present invention.

FIG. 6 schematically represents the in vivo implantation and integration of cultured tissue into a living organism whereby development may be facilitated in accordance with the present invention. Two apparatuses are shown for this purpose within the figure; 2-dimensional grid array 660 (an array of emitters and detectors), and a 3-dimensional multi-surface depth emitter and detector probe 650. Grid array 660 has leads 665 while probe array 650 has leads 655. Intervention zones 630 are the designated sites requiring tissue repair or development. Intervention sites 630 sites may be damaged or otherwise insufficient areas of brain 600 at which immature cells are implanted. Alternatively cells native to or which have migrated to these areas by natural means may be responsive to stimuli from grid array 660 or probe array 650. Grid array 660 is best suited for governing the behavior of developing tissue on surfaces of brain 600, while probe array 650 is best for reaching sub-surface areas of tissue development. In an alternative embodiment, 600 may instead represent another organ of the body other than the brain. Shown in both intervention zones 630 are Type I cells 620 and 640 (implanted), and Type II cells 625 and 645 (implanted or native). In an alternative embodiment, the discrete channels of communication may be a non-native chemical or molecular substance. For example, neurons may be sensitized to an arbitrary molecule which does not naturally function to affect a neuron. This may be accomplished, for example, by gene insertion for a receptor for this arbitrarily selected molecule, with the receptor functionally tied to the desired output function of that cell type. In this new configuration, whenever that arbitrary molecule is introduced into the culture, that cell will react. In the example of a neuron, it would fire an action potential, or alternatively, become hyperpolarized. Because no other type of cell in the milieu is sensitive to the selected molecule, astrocytes and endothelial cells do not react.

Another aspect of the patent invention is directed to use and introduction of a microbial opsin into embryonic stem cells to develop optogenetic technology for stem cell engineering applications, with a novel automated system for noninvasive modulation of embryonic stem cell differentiation employing fast optics and optogenetic control of ion flux.

In one experimental embodiment, mouse embryonic stem cells (ESCs) were stably transduced with ChR2-YFP and purified by FACS. Illumination of resulting ChR2-ESCs with pulses of blue light triggered strong inward currents. These labeled ESCs retained the capability to differentiate into functional mature neurons, assessed by the presence of voltage-gated sodium currents, action potentials, fast excitatory synaptic transmission, and expression of mature neuronal proteins and morphology. Optically stimulating ChR2-ESCs during the first 5 days of neuronal differentiation, with high-speed optical switching on a custom robotic stage and environmental chamber for integrated optical stimulation and automated imaging, drove increased expression of neural markers. These data point to potential uses of ChR2 technology for chronic and temporally precise noninvasive optical control of embryonic stem cells both in vitro and in vivo, ranging from noninvasive control of stem cell differentiation to causal assessment of the specific contribution of transplanted cells to tissue and network function.

As another aspect of the present invention and useful alone or in combination with other aspects disclosed herein, optogenetic technology (e.g., as described herein) may be used to selectively affect certain cell types, rendering target cell types sensitive to light while other cell types remain insensitive to light. In this manner, such a system effectively differentiates between various cell types. In this regard, development of one cell type can be distinguished from other cell types by creating a viral vector in which a cell-type-specific promoter gene sequence sits immediately adjacent to the portion which codes for an opsin such as ChR2 or NpHR. As specific examples, glial cells may be targeted by use of a GFAP promoter; neurons in general by a Synapsin-I promoter; excitatory neurons by a CaMK2-alpha promoter; inhibitory neurons by a VGAT promoter; endothelial cells by a TIE-1 promoter, and stem cells including progenitor cells by a nestin promoter.

EXPERIMENTAL RESULTS

Transduction of Mouse ESCs with ChR2

Figure 7:
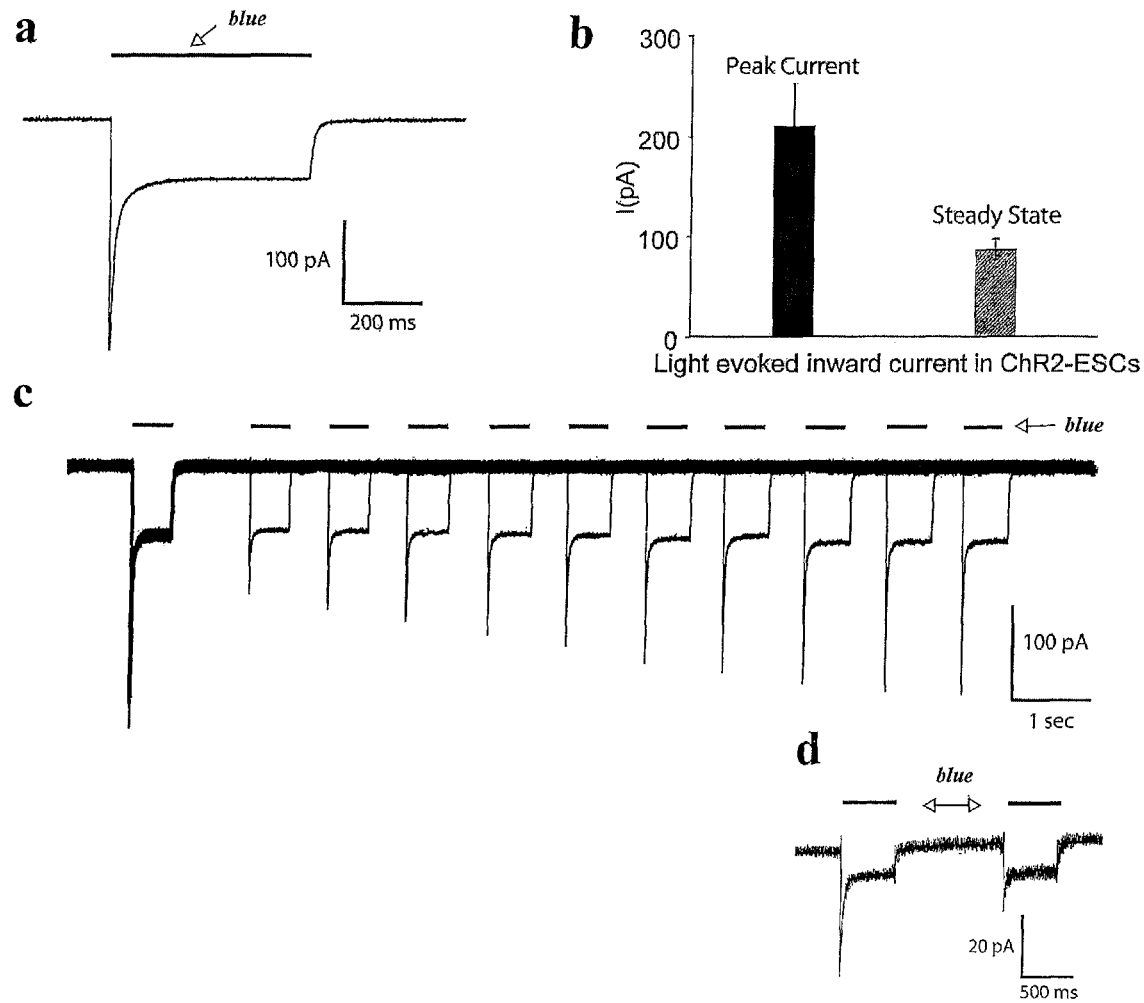
FIGS. 7-11 depict images and charts showing results of experimental implementations in accordance with the present invention.

To assess the potential of optogenetics in stem cells, mouse ESCs were transduced with a lentiviral ChR2-YFP-construct under the control of the EF1a promoter; after sorting for the top 5% based on YFP fluorescence intensity, we found that the population doubling time and vitality of the resulting ChR2-YFP-ESCs did not differ significantly compared to non-transduced ESCs (not shown), and confocal microscopy demonstrated membrane localization of ChR2-YFP with high, uniform expression levels in the ESC population. ChR2-ESCs continued to express the embryonic stem cell marker SSEA1 and Oct4 (not shown), maintaining the undifferentiated state as did non-transduced control cells. Electrophysiologically, the ChR2-ESCs displayed typical outwardly rectifying and passive currents, while illumination with blue light (470 nm, 500 ms pulse duration) evoked inward photocurrents (FIGS. 7a, 7b); steady-state photocurrents showed little inactivation while peak photocurrents showed inactivation and recovery with kinetics similar to that previously shown in neurons30 (FIG. 7c).

The microbial opsins, including ChR2, require a chromophore (all-trans-retinal) to absorb incoming blue photons and gate the conformational change of the protein. A surprising finding in the development of microbial opsins for neurobiology was that mammalian neurons (but not invertebrate neurons) appear to have sufficient endogenous retinoids to allow ChR2 to function without addition of any chemical cofactors. If optogenetics is to become a useful tool in stem cell engineering, it will be important to determine in stem cells the extent of dependence on exogenous chemicals like retinoids both in vitro and in vivo. No retinoids were added for the in vitro experiments described above; to further determine dependence or independence from exogenous retinoids in vivo, 5×105 ChR2-YFP expressing ESCs were stereotaxically injected into the cortex of healthy rats. One week after transplantation, animals were sacrificed and in acute slices, transplanted cells could be identified by YFP fluorescence. To test whether transplanted ChR2-ESCS could still respond to optical Stimulation, patch clamp recordings were conducted, revealing inward currents upon illumination with blue light (FIG. 7d) that displayed typical inactivation of the peak current and stability of the steady-state current. Together these data demonstrate that optogenetic interventions can be effective, well-tolerated, and independent of exogenous chemical cofactors in mammalian ES cells.

Differentiation of ChR2-ESCs

Intracellular $Ca^{2+}$ is a major mediator of differentiation and survival in stem cells and their progeny, especially in neural lineages. ChR2 itself is a nonselective cation channel that directly allows $Ca^{2+}$ entry into cells. Additional routes of photo-evoked $Ca^{2+}$ entry could include activation of voltage-gated $Ca^{2+}$ channels (VGCCs) by virtue of ChR2-induced membrane voltage changes. Notably, we find that mouse ES cells express four major VGCCs assessed by RTPCR and immunoreactivity (FIGS. 8a, 8b), and this supplementary mechanism for photoactivated $Ca^{2+}$ entry could become increasingly potent as cells proceed down the neuronal lineage and develop hyperpolarized membrane potentials. Regardless, the known $Ca^{2+}$ flux of ChR2 itself suggested the potential for optical control of stem cell processes.

Figure 8:
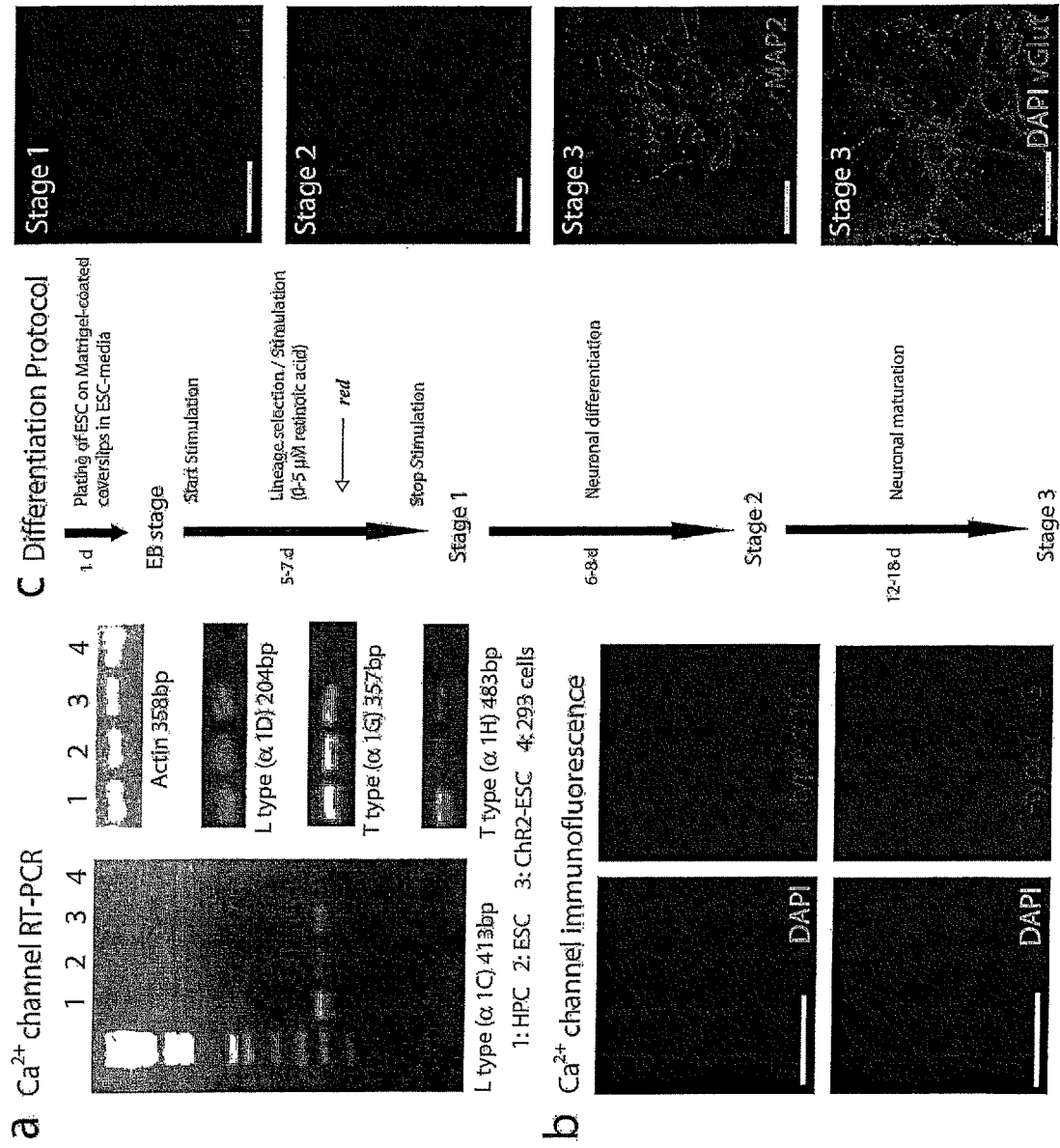
Figure 9:
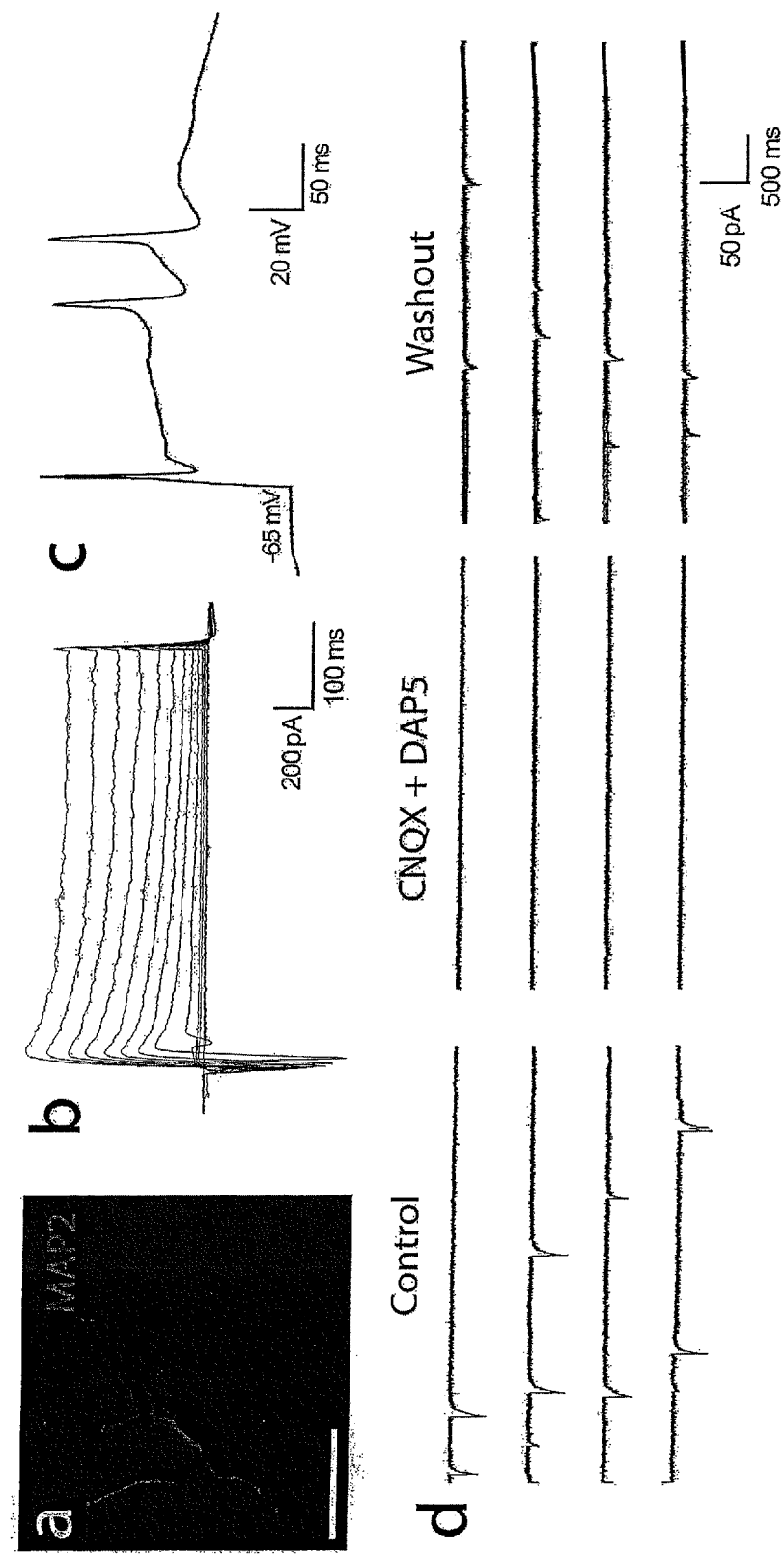

We first verified that ChR2-ESCs were capable of neural lineage differentiation, using a retinoic acid-based neural differentiation protocol (FIG. 8c). At differentiation day 8, 40±10% of the cells expressed the neural lineage marker nestin. By day 14, a dense network of β-3-tubulin-positive ESC-derived immature neurons could be detected, followed by expression of the mature neuronal cytoskeletal protein MAP2 and the vesicular glutamate transporter II (vGlutll). By day 28 the resulting ChR2-ESC-derived neurons displayed mature neuronal morphology, sodium currents, action potentials, and excitatory postsynaptic currents which could be blocked by excitatory synaptic transmission glutamate receptor antagonists CNQX and D-AP5 (FIG. 9a-d).

Optical Modulation of Neural Differentiation

One challenge in deriving replacement tissues from ES cells is that the cell-type specification and phenotype consolidation processes, and therefore also the patterning and differentiation stimuli, take place over many days; to be applicable, optogenetic stimulation must therefore be deliverable in chronic fashion. In designing the system to meet this challenge, it is also important to consider that since knowledge of the precise combinations and timing of signaling events required for stem cell differentiation is limited, a multiwall configuration would in principle be desirable, to allow for fast optical mapping of cell lines, conditions, and "differentiation space" in the laboratory. We therefore devised an automated multiwell optogenetic stimulation approach designed to precisely revisit and optically stimulate multiple regions of interest (ROIs) in defined patterns over extended periods of time (FIG. 10a).

Figure 10:
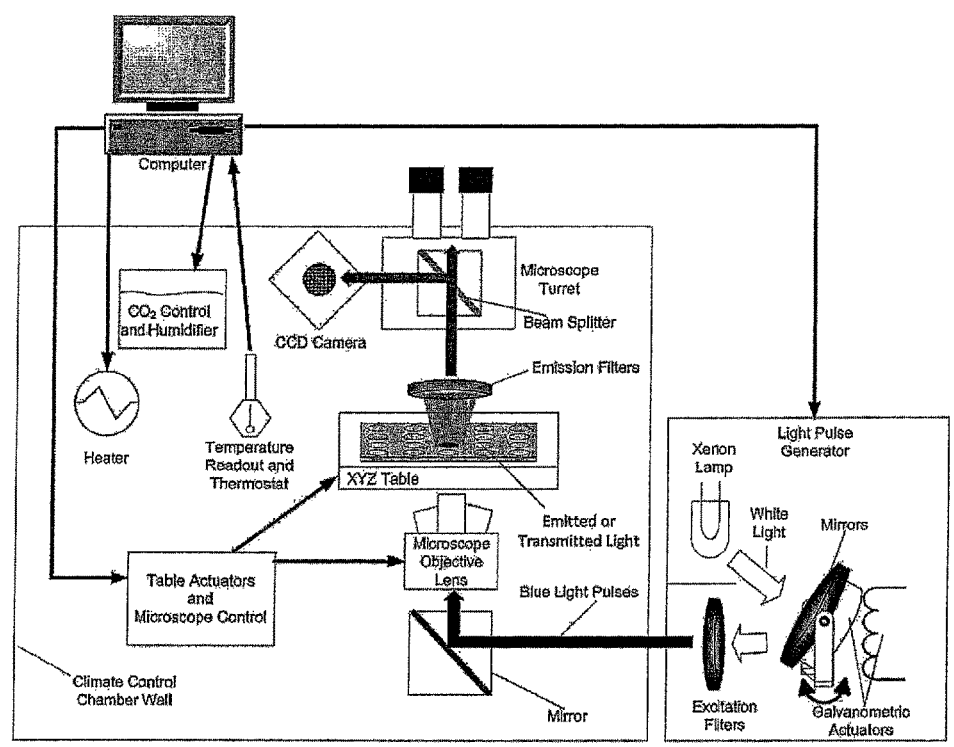
Figure 10:
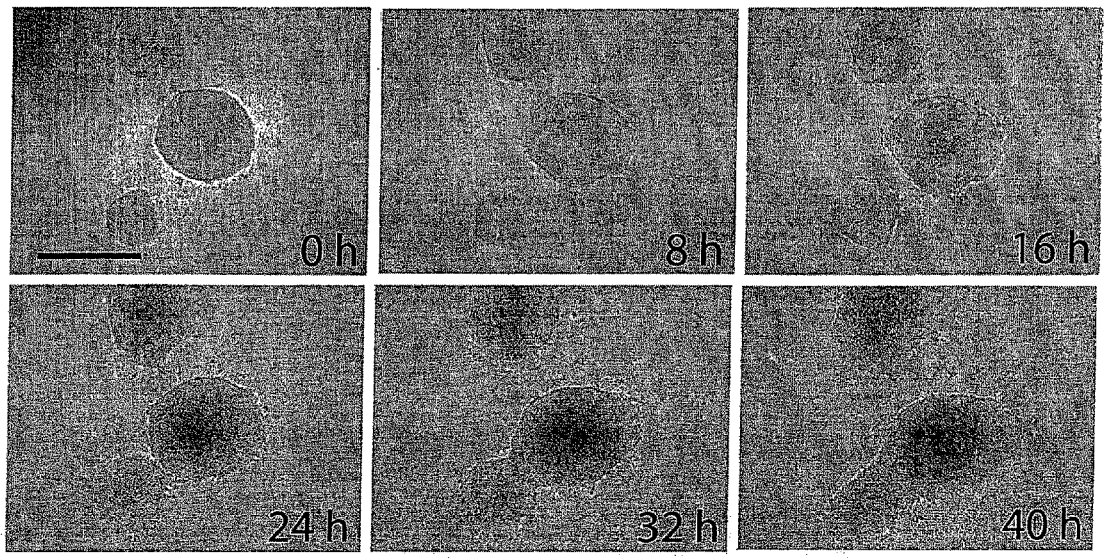

ROIs in multiwell plates were user-defined in a custom GUI and their locations saved for rapid and reproducible access by a robotic stage (FIG. 10a). Stimulation parameters (excitation filter wavelength, optical switch pulse duration, and frequency/duty cycle of excitation) were set per configured parameters via the software-based equipment that controls the microscopic stage in the three spatial dimensions, and controls operation of the DG-4 optical switch which employs spinning galvanometers to deliver light with sub-millisecond precision (FIG. 10a). The microscope itself is surrounded by a climate controlled Plexiglass chamber wherein both temperature and $CO_2$-level are tightly regulated and temporally precise imaging can proceed in parallel with optical stimulation (FIG. 10a). Embryonic stem cells can be cultured and photo stimulated in this environment rather than in a standard incubator for many weeks, allowing us to investigate the effect of optogenetic stimulation on the differentiation of embryonic stem cells in a controlled, reproducible manner.

In a typical experiment, ESCs were seeded in a 24 well plate, at a density of 100,000 cells/ml and 1 ml/well. To directly capitalize on the advantages of the multiwall plate format, certain wells were seeded with native ESCs and others with ChR2-YFP ESCs; moreover specific wells were programmed to receive optical stimulation; finally, in combinatorial fashion, different wells within groups received different concentrations of differentiation factors (for example, the neural lineage factor retinoic acid at 0, 1, or 2.5 μM). In this way differentiation space could be efficiently mapped while controlling for nonspecific effects related to the rig or to illumination. Cells were stimulated for 5 days with blue light (470 nm at 15 Hz for 10 s) delivered every 60 min using a 10× objective. The survival and morphology of the cells was monitored using time-lapse imaging every 8 hours (FIG. 10b-g), also demonstrating the precision and accuracy of the automated setup in its ability to precisely revisit the same ROI.

Figure 11:
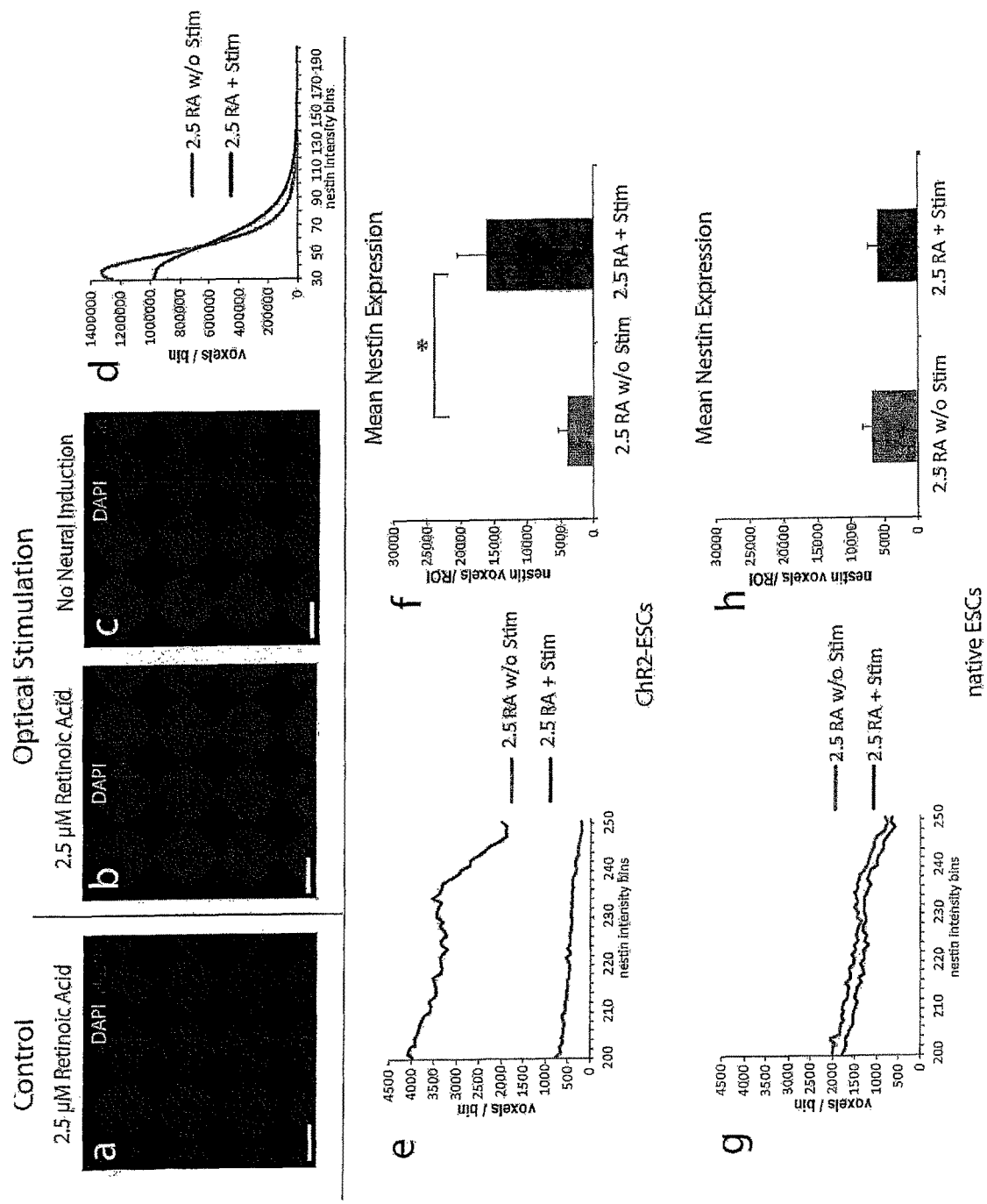

To identify rapidly-acting effects of optical stimulation on ESC differentiation, cells were simultaneously assayed following the conclusion of stimulation (FIG. 8c). Immunostaining for the neural marker nestin followed by confocal analysis of fluorescence histograms was used to quantify neural lineage differentiation, along with imaging of cellular nuclei using DAPI. FIGS. 11a and 11b show a 3D projection of two typical confocal z-stacks of single ROIs, displaying both DAPI (blue) and nestin (red) fluorescence. Optically stimulated cells consistently showed higher nestin immunoreactivity (FIG. 11b) compared to non-stimulated cells (FIG. 11a), while optical stimulation interestingly was ineffective in the absence of retinoic acid (RA) (FIG. 11c). To quantify this effect, we generated fluorescence intensity histograms of all ROIs across all wells in each condition (resulting in more than 150 confocal images per condition). These intensity histograms revealed considerable differences between stimulated and nonstimulated ChR2-ESCs (FIG. 11d-h; $p<0.01$, Kolmogorov-Smirnov test). We next conducted an experiment to test the possibility that the nestin distributions of unmodified ("native") optically stimulated ESCs (FIG. 5g) and ChR2-YFP optically stimulated ESCs (FIG. 11e) could represent samples from the same distribution; after automated optical stimulation, repeated as in the above experiment and subsequent blinded analysis, we found that this hypothesis could be rejected ($p<0.001$; two-tailed K-S $Z=5.43$; FIG. 11e,g shows the observed increase in high levels of optically-induced nestin expression in the ChR2-YFP cells). We calculated the mean nestin fluorescence intensity in each condition, and comparing optically stimulated with non-optically stimulated cells across all conditions revealed that only C hR2-YFP ESCs incubated with 2.5 pM RA showed a significant optogenetically-induced increase in mean nestin expression ($p<0.01$, two-tailed t-test; FIGS. 11f, 11h). In the presence of 1 μM RA, a nonsignificant trend toward higher nestin expression in the setting of optical stimulation was observed, while in 0 μM RA no effect of optical stimulation was observed (e.g., FIG. 11c).

Accordingly, the present invention presents an application of optical control technology to stem cell engineering, and demonstrates the potential of the optogenetic approach by successfully expressing and driving the light-gated cation channel channelrhodopsin-2 in mouse embryonic stem cells. We found that ChR2-YFP ESCs were viable and maintained the undifferentiated state, and also retained the capability to generate electrophysiologically mature neurons when differentiated. Moreover, pulsed illumination with blue light evoked precise and robust cation currents in ESCs, enabling reproducible and predictable control of ion flux without requiring addition of chemical cofactors either in vitro or within intact brain tissue. By developing automated multiwell optogenetic stimulation tools, we were able to deliver optical stimulation in combinatorial experiments over extended periods of time with high spatiotemporal precision, and found that optogenetic stimulation could modulate neural lineage progression in the presence of 2.5 μM RA.

As specifically discussed in connection with the underlying provisional documents, depolarization has been reported in other studies to modulate neural differentiation processes in dividing cells, and indeed depolarization and calcium waves have both been observed in proliferating GNS progenitors in situ; for example, in early CNS development, Momose-Sato et al. demonstrated spontaneous depolarization waves, and Kriegstein and colleagues observed calcium waves in cortical progenitors. Likewise in postmitotic neurons, depolarization plays additional important roles in CNS development, affecting spine development and synaptic plasticity. In connection with the present invention, it is now believed that while the specific signal transduction cascades mediating the influence of membrane depolarization events in early development remains unclear, the $Ca^{2+}$ and $Ca^{2+}$ channels may play a key role and ChR2 is well suited to recruit these mechanisms. Emerging evidence points to the expression of VGCCs during early stages of embryonic, and in accordance with aspects of the present invention, this allows ChR2 to recruit $Ca^{2+-}$ dependent cellular processes not only via its own light-activated $Ca^{2+}$ flux but also by activating native VGCCs as differentiating cells mature. According to other aspects, lineages arising from ESCs also are to be modulated by $Ca^{2+}$, including cardiac cells and others reporting on enhancement of hematoendothelial differentiation upon chronic depolarization of human ESCs). In all of these cases, as we observed with the RA gating of optogenetic modulation, depolarization or $Ca^{2+}$ influx is a function of other patterning and lineage-specific differentiation factors.

Recent studies have shown the induction of pluripotent stem cells (iPS) from somatic cell, significantly expanding the possible sources of stem cells in regenerative medicine but further highlighting the ongoing need for selective and highly sensitive stem cell differentiation and control tools. Globally applied stimuli such as growth factors and organic compounds will affect all cells present, including non-dividing constituents of the stem cell niche as well as the stem cells and their progeny, but it is unlikely that these growth factors will have the same desired effect in all of the very different cells present in the typical differentiation milieu. By targeting optical control to either the proliferating cells or to niche constituents like astrocytes, optogenetic control of intracellular signaling will allow selective control of the desired cell type.

Indeed, this optical specificity principle extends to the selective control of fully differentiated stem cell progeny in situ. Minimally invasive fiberoptic strategies have brought optogenetics to the fully intact, behaving mammal. Transplanted cells may require electrical activity to drive the final stages of phenotype consolidation and to fully integrate into host neural circuitry, representing the central goal of stem cell based regeneration medicine.

Compared to conventional electric stimulation or drugs, the genetic targeting of ChR2 makes it possible to specifically and reversibly drive precise amounts of activity in the transplanted ESCs and their progeny, which moreover do not require addition of chemical cofactors in vivo for ChR2 function. Finally, optically driving only the transplanted cells, with behavioral readouts or non-invasive imaging readout modalities like fMR1 (and without the serious problem of signal interference from metal electrodes), opens the door to imaging and tuning the specific contribution of transplanted cells in the restoration of network activity and circuit dynamics, for example in Parkinson's disease. With these approaches and others, optogenetic technologies are applicable as valuable tools in stem cell biology and regenerative medicine.

Experimental Methods

Mouse Embryonic Stem Cell Culturing

Mouse embryonic stem cells (CRL-1934, ATCC, Manassas, USA) were grown in DMEM medium (ATCC) containing medium conditioned by feeder cells (CRL-1503, ATCC), 15% fetal calf serum (Gibco), 15 ng/ml leukemia inhibitory factor (LIF; Sigma-Aldrich), 0.1 mM 2-mercaptoethanol (Sigma-Aldrich), and 1% penicillin-streptomycin (Sigma-Aldrich). The cells were cultured in 75 $cm^2$ cell culture flasks (Falcon) with 20 ml medium at 37° C. and 5% $CO_2$ and passaged every 3 days. Only undifferentiated cells in suspension were used for the experiments. After washing in phosphate-buffered saline (PBS) (Gibco, Invitrogen), cells were counted in a Neubauer counting chamber. The viability was determined by staining with trypan blue solution (0.4%; Sigma-Aldrich).

Transduction of ESCs with ChR2

Lentiviruses carrying the ChR2-EYFP fusion gene under the control of the EF-1-alpha promoter were generated as previously described. Viruses were concentrated via ultracentrifugation and redissolved in PBS at $\frac{1}{1000}$ of the original volume. The concentrated viruses were then incubated with ESCs for 24 hr and transduction efficiency evaluated using fluorescent microscopy one week after transduction. To obtain a highly and homogenously expressing ChR2-ESC colony, cells were sorted using FACS; a subpopulation consisting of the top 5% of YFP-expressing cells was collected.

Neuronal Differentiation of Embryonic Stem Cells

Neuronal differentiation was performed as previously described, with modifications. ESCs were plated on matrigel-coated dishes in embryoid body stage in complete ESC medium (see above). 24 hours later, medium was changed to ESC medium lacking LIF and including 5 µM retinoic acid, and changed every second day for 5 days. As a second differentiation step, cells were incubated with neural expansion medium for 7 days consisting of N2 supplement, SHH (50 ng/ml), FGF-8b (100 ng/ml), bFGF (10 ng/ml) and ascorbic acid (200 µM, Sigma) in DMEM/F12 and changed every two days. Thereafter cells were cultured in N2 and ascorbic acid in DMEM/F12.

Immunohistochemical Staining of Cultured Cells

Cells were fixed with 4% paraformaldehyde in PBS for 30 min at room temperature. Fixation was stopped by washing cells three times with 0.1M glycine/PBS. Cells were permeabilized and blocked (4% BSA/0.4% saponin/PBS) for 30 min and incubated in primary antibody solution at 4° C. overnight. Cells were washed 4 times and incubated with secondary antibody at room temperature for 2 hr. Cells were washed 3× with PBS, and at the final washing step DAP1 was added (1:50,000). Coverslips were mounted using anti-quenching Fluoromount. Primary antibodies were mouse anti-SSEA1 (Chemicon 1:300), mouse anti-nestin (Chemicon 1:200), chicken anti-βill tubulin (Chemicon 1:200), mouse anti MAP2ab (Sigma 1:500), rabbit anti vGlut 2 (Chemicon 1:200), and rabbit anti-a1C, -a1D, -a1G, and -a1H (all Alomone labs; 1:200). Cy3 or Cy5 conjugated donkey anti mouse, chicken and rabbit secondary antibodies (Jackson) were all used at 1:200.

RT-PCR

Cells were homogenized by Homogenizer (Invitrogen). RNA isolation was performed using Micro-to-Midi Total RNA Purification System (Invitrogen). Prior to RT-PCR, RNA samples were pretreated with DNaseI (Invitrogen) and reverse transcription conducted per manufacturer's protocol. Negative controls without reverse transcriptase did not result in amplified sequences. Mouse hippocampal total RNA was purchased from Clontech and the resulting cDNA served as a positive control. For PCR analysis, primers targeted to coding regions of two subunits each from both the L- and T-type VGCC families were used, as follows: L-type a1C Forward: GTGGTTAGCGTGTCCCTCAT Reverse: GTGGAGACGGTGAAGAGAGC; L-type a1D F: AATGGCACGGAATGTAGGAG R: GACGAAAAATGAGCCAAGGA; T-type a1G F: CTGAGCGGATCTTCCTAACG R: TGAAAAAGGCACAGCAGATG; T-type a1H F: TGGGAACGTGCTTCTTCTCT R: TGGGCATCCATGACGTAGTA; Housekeeping gene (Actin) F: GGCATTGTGATGGACTCCGG R: TGCCACAGGATTCCAT- ACCC. 293 FT kidney cells did not express these channel subunits, as expected (FIG. 8a), and PCR products of actin and L-type and T-type subunits were cloned and sequenced to confirm identity.

Long-Term Optical Stimulation of ESCs

Key components of the hardware interface include (a) Oasis4i Controller (Objective Imaging) (hardware for x-y-z 3-axis and focus control) (http://ww.objectiveimaging.com/Download/OI_Download.htm—software development kit (SDK) for the Oasis4i Controller), (b) DG4 Ultra High Speed wavelength switcher (Sutter), (c) Retiga SRV Camera (Qimaging), and (d) Leica DM6000 Microscope controlled by AHM (Abstract Hardware Model) controller. The parallel port is controlled using DLPORTIO library file (www.driverlinx.com/DownLoad/DIPortIO.htm—Dlls to for parallel port control) and camera parameters (gain, exposure) set using QCam SDK (Ver. 5.1.1.14) (http://ww.qimaging.com/support/downloads/—SDK to control the Retiga SRV/Exi Cameras). The custom software user interface to the optogenetic stimulation setup was developed using the Microsoft Foundation Library (MFC; Ver. 8.0) and is available on request. Briefly, regions of interest (for example, an embryoid body or a small well in a multiwall plate) to be stimulated and/or imaged are selected using the Oasis4i Controller, and their locations saved using the MFC interface. Stimulation parameters (excitation filter wavelength, the duration of the excitatory pulse, and the frequency and duty cycle of excitation) are then set in the custom GUI. To allow stimulation space to be mapped, each region of interest can be readily programmed to receive a different stimulus pattern to operate over the many days of stimulation and imaging. Similarly, imaging parameters can also be varied for selected regions, including number of images per region and exposure, gain, excitation and emission filters.

Undifferentiated cells were seeded on matrigel (BD) coated coverslips in 24-well plates in complete ESC medium at a density of 100,000 cells/well. Both native ESCs and ChR2-expressing ESCs were used in different wells on the same plate. 24 hours after seeding, medium was changed to the various experimental conditions including complete ESC medium, ESC medium lacking both LIF and conditioned media from feeder cells (differentiation medium), differentiation medium with 1 µM retinoic acid (RA) (Sigma), and differentiation medium with 2.5 µM RA. Optical stimulation was conducted using the previously-described tools (FIG. 4). Up to 30 regions of interest (ROIs) were defined per well, ensuring that all cell-containing regions on the coverslip were stimulated. ROIs were illuminated every hour around the clock over 5 days with blue light (470 nm) pulsing at 15 Hz for 10 s, using a 10× objective (NA 0.3). Every 8 hours, a photomicrograph was programmed to be taken of the selected ROIs. At the end of the experiment, coverslips were removed from the plates and immediately fixed with paraformaldehyde and stained as described above. Mounted slides were labeled with coded numbers by a colleague so that the investigators conducting confocal analysis were blind to treatment condition.

Confocal Microscopy and Image Analysis

Confocal imaging was conducted using the Leica SP2 confocal microscope and a 40× oil objective (NA 0.75). For DAP1 excitation, a 402 nm diode laser was used; Cy5-nestin was excited using a 633 nm HeNe laser. 6 ROIs were randomly and blindly selected for analysis per coverslip, and 1024×1024 8-bit confocal images were obtained. For each ROI, a z-stack with 8-12 x-y-sections and a z step size of 0.98 µm were collected, thereby including all cells present in the ROI. Data analysis was conducted using ImageJ (NIH, USA) software, and after unblinding, confocal images of all ROIs of all coverslips of each condition (e.g., ChR2-ESCs, optically stimulated, 2.5 µM RA) were converted into a single z-stack. Fluorescence intensity histograms were calculated for DAP1 and nestin channels. DAP1 histograms reflecting the cell numbers allowed for a normalization of nestin histograms. All nestin voxel numbers have been divided by this DAP1 factor. Statistical analysis was conducted using SPSS (Chicago, USA) software. To statistically compare histograms, the parameter-free Kolmogorov-Smirnov test was employed, and to compare means, statistical significance was calculated using the t-test.

Stereotactic Cell Transplantation

Rats (male Wistars, 250-350 g) were the subjects of these experiments. Animal husbandry and all aspects of experimental manipulation of our animals were in strict accord with guidelines from the National Institute of Health and approved by members of the Stanford Institutional Animal Care and Use Committee. Rats were anaesthetized by i.p. injection (90 mg ketamine and 5 mg xylazine per kg of rat body weight). For cell transplantation, a 1 mm craniotomy was drilled over motor cortex. 1 µl, of ESCs expressing ChR2-EYFP fusion protein at a density of 50 k cells/µL, suspended in PBS were injected (26 g Hamilton Syringe) into rat motor cortex (AP+1.5 mm, ML+1.5 mm, DV+1.5 mm). The injection duration was 10 min; an additional 10 min delay followed before syringe withdrawal, and electrophysiology was conducted after 1 week.

Electrophysiology

For acute slice electrophysiological experiments, 1 week post cell transplantation, 250 µm cortical slices were prepared in ice-cold cutting buffer (64 mM NaCl, 25 mM NaHCO$_3$, 10 mM glucose, 120 mM sucrose, 2.5 mM KCl, 1.25 mM NaH$_2$PO$_4$, 0.5 mM CaCl$_2$ and 7 mM MgCl$_2$, equilibrated with 95% O$_2$/5% CO$_2$) using a vibratome (VT 1000 S; Leica). After a recovery period of 30 min in cutting buffer at 32-35° C., slices were gently removed to a recording chamber mounted on an upright microscope (DM LFSA, Leica) and continuously perfused at a rate of 3-5 ml/min with carbonated ACSF (124 mM NaCl, 3 mM KCl, 26 mM NaHCO$_3$, 1.25 mM NaH$_2$PO$_4$, 2.4 mM CaCl$_2$, 1.3 mM MgCl$_2$, 10 mM Glucose), ventilated with 95% O$_2$/5% CO$_2$.ChR2-YFP-ESCs were identified on an upright fluorescence microscope (DM LFSA, Leica) with a 20×, 0.5 NA water immersion objective and a YFP filter set. Images were recorded with a CCD camera (Retiga Exi, Qimaging) by Qimaging software. Electrophysiological recordings in cultured ChR2-YFP ESCs were performed as previously described, in Tyrode solution containing (in mM) NaCl 125, KCI 2, CaCI$_2$ 3, MgCI$_2$ 1, glucose 30 and HEPES 25 (pH 7.3 with NaOH). Membrane currents were measured with the patch-clamp technique in whole-cell mode using Axon Multiclamp 700B (Axon Instruments) amplifiers. Pipette solution consisted of (in mM): 97 potassium gluconate, 38 KCl, 6 NaCl, 0.35 sodium ATP, 4 magnesium ATP, 0.35 EGTA, 7 phosphocreatine and 20 HEPES (pH 7.25 with KOH). Pipette resistance was 4-8 MΩ. Membrane potential was noted at the time of establishing the whole cell configuration. We employed pClamp 9 acquisition software (Axon Instruments), a DG-4 high-speed optical switch with 300 W xenon lamp (Sutter Instruments) and a GFP filter set (excitation filter HQ470/40x, dichroic Q495LP; Chroma) to deliver blue light for ChR2 activation. Through a 20× objective lens, power density of the blue light was 8-12 mW/mm$^2$, measured by power meter (Newport). All experiments were performed at room temperature (22-24° C.).

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention, which is set forth in the following claims.

What is claimed is:

1. A method for selectively controlling growth and development of a mammalian stem cell in vivo or in a tissue in vitro, the method comprising:
   a) genetically modifying a selected type of stem cell to express a microbial opsin;
   b) stimulating the genetically modified stem cell with a light-based activation signal, wherein the light-based activation signal is generated by a system comprising:
      i) a light source;
      ii) a pulse generator that is configured to send signals to and control the light source;
      iii) a signal receiver that is configured to receive response signals from the genetically modified stem cell; and
      iv) a computer that is configured to modulate signals sent by the pulse generator based on the response signals;
   c) receiving one or more response signals from the genetically modified stem cell; and
   d) modulating the light-based activation signal based on the response signals, thereby selectively controlling growth and development of the genetically modified stem cell.

2. The method of claim 1, wherein the genetically modified stem cell is present in the brain.

3. The method of claim 1, further including facilitating cellular growth of the stem cell within a predetermined spatial configuration.

4. The method of claim 1, further including facilitating growth of the stem cell within a predetermined geometric configuration.

5. The method of claim 1, wherein the stem cells are neuronal stem cells.

6. The method of claim 1, wherein the genetically modified stem cell is a neural stem cell, and wherein the method further comprises:
   genetically modifying a glial cell to express a second microbial opsin; and
   inducing the glial cell to release nerve growth factor to the neural stem cell by activating the second microbial opsin using direct pulses of illumination.

7. The method of claim 1, wherein the stem cell is an induced pluripotent stem cell.

8. The method of claim 1, wherein the stem cell is a neural stem cell.

9. The method of claim 1, wherein the microbial opsin is channelrhodopsin-2.

10. The method of claim 1, wherein the in vitro tissue is an artificial tissue.

11. The method of claim 10, wherein the artificial tissue comprises cells within an artificial matrix.

12. The method of claim 10, further comprising implanting the artificial tissue in vivo.

13. The method of claim 1, wherein the genetically modified stem cell is present in a tissue in vivo, and wherein the light source is an implantable light source.

14. The method of claim 1, wherein the microbial opsin is encoded by a nucleotide sequence operably linked to a cell type-specific promoter.

15. The method of claim 1, wherein the stem cell is a neuronal stem cell, and wherein the microbial opsin is encoded by a nucleotide sequence operably linked to a neuron-specific promoter.

16. The method of claim 6, wherein the second microbial opsin is encoded by a nucleotide sequence operably linked to a glial cell-specific promoter.

17. The method of claim 1, wherein the genetically modified stem cell is stimulated for a period of time of 5 days in the presence of 2.5 µM retinoic acid.

18. The method of claim 17, wherein the genetically modified stem cell is stimulated with light at 15 Hz for 10 seconds every 60 minutes.

* * * * *

UNITED STATES PATENT AND TRADEMARK OFFICE
CERTIFICATE OF CORRECTION

| | |
|---|---|
| PATENT NO. | : 10,711,242 B2 |
| APPLICATION NO. | : 12/997140 |
| DATED | : July 14, 2020 |
| INVENTOR(S) | : Deisseroth et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1043 days.

Signed and Sealed this
Twentieth Day of December, 2022

*Katherine Kelly Vidal*

Katherine Kelly Vidal
*Director of the United States Patent and Trademark Office*